United States Patent
Jochelson et al.

(10) Patent No.: US 10,507,193 B2
(45) Date of Patent: Dec. 17, 2019

(54) ULTRA LOW DOSE DOXEPIN AND METHODS OF USING THE SAME TO TREAT SLEEP DISORDERS

(71) Applicants: Pernix Sleep, Inc., Morristown, NJ (US); ProCom One, Inc., San Marcos, TX (US)

(72) Inventors: Philip Jochelson, San Diego, CA (US); Neil B. Kavey, Chappaqua, NY (US)

(73) Assignees: Currax Pharmaceuticals LLC, Morristown, NJ (US); ProCom One, Inc., Steamboat Springs, CO (US)

( * ) Notice: Subject to any disclaimer, the term of this patent is extended or adjusted under 35 U.S.C. 154(b) by 0 days.

(21) Appl. No.: 15/911,832

(22) Filed: Mar. 5, 2018

(65) Prior Publication Data

US 2018/0193302 A1 Jul. 12, 2018

Related U.S. Application Data

(63) Continuation of application No. 14/045,645, filed on Oct. 3, 2013, now Pat. No. 9,907,779, which is a continuation of application No. 12/446,914, filed as application No. PCT/US2007/082569 on Oct. 25, 2007, now abandoned.

(60) Provisional application No. 60/854,399, filed on Oct. 25, 2006, provisional application No. 60/873,056, filed on Dec. 6, 2006, provisional application No. 60/910,586, filed on Apr. 6, 2007.

(51) Int. Cl.
| | |
|---|---|
| A61K 31/335 | (2006.01) |
| A61K 9/20 | (2006.01) |
| A61K 9/28 | (2006.01) |
| A61K 31/343 | (2006.01) |
| A61K 31/4162 | (2006.01) |
| A61K 31/437 | (2006.01) |
| A61K 31/4535 | (2006.01) |
| A61K 31/4985 | (2006.01) |
| A61K 31/505 | (2006.01) |
| A61K 31/55 | (2006.01) |
| A61K 45/06 | (2006.01) |

(52) U.S. Cl.
CPC .......... *A61K 31/335* (2013.01); *A61K 31/343* (2013.01); *A61K 31/4162* (2013.01); *A61K 31/437* (2013.01); *A61K 31/4535* (2013.01); *A61K 31/4985* (2013.01); *A61K 31/505* (2013.01); *A61K 31/55* (2013.01); *A61K 45/06* (2013.01); *A61K 2300/00* (2013.01)

(58) Field of Classification Search
None
See application file for complete search history.

(56) References Cited

U.S. PATENT DOCUMENTS

| | | |
|---|---|---|
| 3,420,851 A | 1/1969 | Bloom et al. |
| 3,438,981 A | 4/1969 | Stach |
| 3,509,175 A | 4/1970 | Tretter |
| 4,110,438 A | 8/1978 | Gahwyler |
| 4,434,171 A | 2/1984 | Müller |
| 4,833,154 A | 5/1989 | Jean-Louis et al. |
| 5,030,632 A | 7/1991 | Sterling |
| 5,116,852 A | 5/1992 | Gammans |
| 5,332,661 A | 7/1994 | Adamczyk et al. |
| 5,502,047 A | 3/1996 | Kavey |
| 5,585,115 A | 12/1996 | Sherwood et al. |
| 5,643,897 A | 7/1997 | Kavey |
| 5,725,883 A | 3/1998 | Staniforth et al. |
| 5,725,884 A | 3/1998 | Sherwood et al. |
| 5,733,578 A | 3/1998 | Hunter et al. |
| 5,741,524 A | 4/1998 | Staniforth et al. |
| 5,858,412 A | 1/1999 | Staniforth et al. |
| 5,866,166 A | 2/1999 | Staniforth et al. |
| 5,948,438 A | 9/1999 | Staniforth et al. |
| 5,965,166 A | 10/1999 | Hunter et al. |
| 6,103,219 A | 8/2000 | Sherwood et al. |
| 6,106,865 A | 8/2000 | Staniforth et al. |
| 6,211,229 B1 | 4/2001 | Kavey |
| 6,217,907 B1 | 4/2001 | Hunter et al. |
| 6,217,909 B1 | 4/2001 | Sherwood et al. |
| 6,219,674 B1 | 4/2001 | Classen |
| 6,344,487 B1 | 2/2002 | Kavey |
| 6,358,533 B2 | 3/2002 | Sherwood et al. |
| 6,391,337 B2 | 5/2002 | Hunter et al. |
| 6,395,303 B1 | 5/2002 | Staniforth et al. |
| 6,403,597 B1 | 6/2002 | Wilson et al. |
| 6,407,128 B1 | 6/2002 | Scaife et al. |
| 6,471,994 B1 | 10/2002 | Staniforth et al. |
| 6,521,261 B2 | 2/2003 | Sherwood et al. |
| 6,584,472 B2 | 6/2003 | Classen |
| 6,683,102 B2 | 1/2004 | Scaife et al. |
| 6,746,693 B2 | 6/2004 | Staniforth et al. |
| 6,852,336 B2 | 2/2005 | Hunter et al. |
| 6,858,231 B2 | 2/2005 | Sherwood et al. |
| 6,866,867 B2 | 3/2005 | Staniforth et al. |
| 6,936,277 B2 | 8/2005 | Staniforth et al. |
| 7,135,196 B2 | 11/2006 | Stockham |
| 7,179,488 B2 | 2/2007 | Sherwood et al. |
| 7,276,536 B2 | 10/2007 | Urata et al. |
| 7,425,556 B2 | 9/2008 | Chapdelaine et al. |
| 7,452,872 B2 | 11/2008 | Johnson |
| 7,465,795 B2 | 12/2008 | Chapdelaine et al. |

(Continued)

FOREIGN PATENT DOCUMENTS

| | | |
|---|---|---|
| WO | 1999/40898 A2 | 8/1999 |
| WO | 2000/10554 A2 | 3/2000 |

(Continued)

OTHER PUBLICATIONS

Seminar on Psychosomatics, Auspices of Academy of Psychosomatic Medicine, p. 4-63 (1968).

(Continued)

*Primary Examiner* — Olga N Chernyshev
(74) *Attorney, Agent, or Firm* — Servilla Whitney LLC

(57) ABSTRACT

The invention relates to doxepin, pharmaceutically acceptable salts and prodrugs of doxepin; compositions containing the same, and the use of any of the aforementioned for the treatment of sleep disorders.

9 Claims, No Drawings

(56) References Cited

U.S. PATENT DOCUMENTS

| | | |
|---|---|---|
| 7,863,296 B2 | 1/2011 | Weiner et al. |
| 7,915,307 B2 | 3/2011 | Casseday et al. |
| 8,097,625 B2 | 1/2012 | Lalji et al. |
| 8,513,299 B2 | 8/2013 | Rogowski et al. |
| 8,598,119 B2 | 12/2013 | Mates et al. |
| 9,107,898 B2 | 8/2015 | Rogowski et al. |
| 9,463,181 B2 | 10/2016 | Dube et al. |
| 9,486,437 B2 | 11/2016 | Rogowski et al. |
| 9,498,462 B2 | 11/2016 | Dube et al. |
| 9,532,971 B2 | 1/2017 | Schioppi et al. |
| 9,572,814 B2 | 2/2017 | Casseday et al. |
| 9,801,847 B2 | 10/2017 | Dubé et al. |
| 9,861,607 B2 | 1/2018 | Rogowski et al. |
| 9,907,779 B2 | 3/2018 | Jochelson et al. |
| 9,907,780 B2 | 3/2018 | Schioppi et al. |
| 10,143,676 B2 | 12/2018 | Dubé et al. |
| 2002/0037828 A1 | 3/2002 | Wilson et al. |
| 2002/0197235 A1 | 12/2002 | Moran |
| 2003/0181353 A1 | 9/2003 | Nyce |
| 2003/0206978 A1 | 11/2003 | Sherwood et al. |
| 2003/0235617 A1 | 12/2003 | Martino et al. |
| 2004/0063721 A1 | 4/2004 | Deecher et al. |
| 2004/0115142 A1 | 6/2004 | Sherwood et al. |
| 2004/0224017 A1 | 11/2004 | Mulye |
| 2004/0265374 A1 | 12/2004 | Staniforth et al. |
| 2005/0013861 A1 | 1/2005 | Sherwood et al. |
| 2005/0118261 A1 | 6/2005 | Oien et al. |
| 2005/0123609 A1 | 6/2005 | Hirsh et al. |
| 2005/0147673 A1 | 7/2005 | Staniforth et al. |
| 2005/0171160 A1 | 8/2005 | Edgar et al. |
| 2005/0196439 A1 | 9/2005 | Sherwood et al. |
| 2005/0214365 A1 | 9/2005 | Yousef et al. |
| 2005/0239838 A1 | 10/2005 | Edgar et al. |
| 2005/0256165 A1 | 11/2005 | Edgar et al. |
| 2006/0008522 A1 | 1/2006 | Staniforth et al. |
| 2006/0228487 A1 | 10/2006 | Schaible et al. |
| 2007/0142328 A1 | 6/2007 | Chapdelaine et al. |
| 2007/0142382 A1 | 6/2007 | Chapdelaine et al. |
| 2007/0281990 A1 | 12/2007 | Rogowski et al. |
| 2008/0058407 A1 | 3/2008 | Baron et al. |
| 2008/0058408 A1 | 3/2008 | Rogowski et al. |
| 2008/0182890 A1 | 7/2008 | Jochelson et al. |
| 2009/0042971 A1 | 2/2009 | Rogowski et al. |
| 2009/0042972 A1 | 2/2009 | Rogowski et al. |
| 2009/0074862 A1 | 3/2009 | Schioppi et al. |
| 2010/0105614 A1 | 4/2010 | Jochelson |
| 2010/0179214 A1 | 7/2010 | Dubé et al. |
| 2010/0179215 A1 | 7/2010 | Dubé et al. |
| 2010/0227916 A1 | 9/2010 | Kavey et al. |
| 2011/0077200 A1 | 3/2011 | Jochelson et al. |
| 2011/0166215 A1 | 7/2011 | Casseday et al. |
| 2011/0178166 A1 | 7/2011 | Rogowski et al. |
| 2011/0318412 A1 | 12/2011 | Schioppi et al. |
| 2012/0088822 A1 | 4/2012 | Rogowski et al. |
| 2012/0245222 A1 | 9/2012 | Rogowski et al. |
| 2013/0005655 A1 | 1/2013 | Jochelson et al. |
| 2013/0041021 A1 | 2/2013 | Casseday et al. |
| 2013/0096188 A1 | 4/2013 | Dube et al. |
| 2013/0102658 A1 | 4/2013 | Dube et al. |
| 2013/0150434 A1 | 6/2013 | Jochelson et al. |
| 2013/0259936 A1 | 10/2013 | Schioppi et al. |
| 2013/0296413 A1 | 11/2013 | Kavey et al. |
| 2016/0030383 A1 | 2/2016 | Rogowski et al. |
| 2017/0157140 A1 | 6/2017 | Casseday et al. |
| 2018/0050010 A1 | 2/2018 | Dubé et al. |
| 2018/0125809 A1 | 5/2018 | Rogowski et al. |
| 2018/0193302 A1 | 7/2018 | Jochelson et al. |
| 2018/0256533 A1 | 9/2018 | Schioppi et al. |

FOREIGN PATENT DOCUMENTS

| | | |
|---|---|---|
| WO | 2000/50025 A1 | 8/2000 |
| WO | 2003/004009 A1 | 1/2003 |
| WO | 2003/047519 A2 | 6/2003 |
| WO | 2003/066029 A2 | 8/2003 |
| WO | 2007/136845 A2 | 11/2007 |
| WO | 2007/142810 A2 | 12/2007 |
| WO | 2007/142811 A2 | 12/2007 |

OTHER PUBLICATIONS

Silenor (doxepin) Prescribing Information. Revised Mar. 2010. p. 1-12.

Sinequan (doxepin HCl) Capsules Oral Concentrate. Prescribing Information. Revised Oct. 2008. p. 1-13.

Somaxon Pharmaceuticals Announces Acceptance for Filing of New Drug Application for Silenor™ for the Treatment of Insomnia, Somaxon Pharmaceuticals Press Release, San Diego, CA, p. 1-5 (Apr. 15, 2008).

Somaxon Pharmaceuticals Announces Completion of 26-Week Transgenic Mouse Carcinogenicity Study of Silenor™, Somaxon Pharmaceuticals Press Release, San Diego, CA, p. 1-3 (Jan. 9, 2008).

Somaxon Pharmaceuticals Announces Data to be Presented at American Psychiatric Association 161st Annual Meeting, Somaxon Pharmaceuticals Press Release, San Diego, CA (May 2, 2008).

Somaxon Pharmaceuticals Announces Data to be Presented at American Psychiatric Association 161st Annual Meeting, Somaxon Pharmaceuticals Press Release, San Diego, CA, p. 1-7 (May 7, 2008).

Somaxon Pharmaceuticals Announces FDA Approval of Silenor® (Doxepin) for the 266 Treatment of Insomnia, Somaxon Pharmaceuticals Press Release, San Diego, CA, p. 1-5 (Mar. 18, 2010).

Somaxon Pharmaceuticals Announces Positive Phase 3 Results with Silenor™ for 267 theTreatment of Adults with Chronic Insomnia, Somaxon Pharmaceuticals, p. 1-5, (Apr. 10, 2006).

Somaxon Pharmaceuticals Announces Positive Results in a Phase II Dose-Finding Study of 268 Low-dose Doxepin in Adults with Primary Sleep Maintenance Insomnia, Somaxon Pharmaceuticals, p. 1-2, (Jan. 6, 2005).

Somaxon Pharmaceuticals Announces Positive Results in a Phase II Dose-Finding Study of Low-Dose Doxepin in Elderly Patients with Primary Sleep Maintenance Insomnia, Somaxon Pharmaceuticals, p. 1-3, (Apr. 21, 2005).

Somaxon Pharmaceuticals Announces Presentation of Phase II Silenor® Data at the Associated Professional Sleep Societies Annual Meeting, Somaxon Pharmaceuticals, p. 1-2, (Jun. 20, 2006).

Somaxon Pharmaceuticals Announces the Completion of Enrollment in a Phase II Study Evaluating S0-101 for the Treatment of Sleep Maintenance Insomnia in Adults, Somaxon Pharmaceuticals, p. 1, (Oct. 7, 2004).

Somaxon Pharmaceuticals Presents Analyses of Silenor Clinical Data at the American Psychiatric Association Annual Meeting, Somaxon Pharmaceuticals Press Release, San Diego, CA, p. 1-6 (May 20, 2009).

Somaxon Pharmaceuticals Presents Pharmacological Data on Doxepin at the 21st European College of Neuropsychopharmacology Congress, Somaxon Pharmaceuticals Press Release, San Diego, CA, p. 1-3 (Sep. 2, 2008).

Somaxon Pharmaceuticals Provides Update on New Drug Application for Silenor® (Doxepin) for the Treatment of Insomnia, Somaxon Pharmaceuticals Press Release, San Diego, CA, p. 1-4 (Apr. 7, 2009).

Somaxon Pharmaceuticals Provides Update on New Drug Application for Silenor® for the Treatment of Insomnia, Somaxon Pharmaceuticals Press Release, San Diego, CA, p. 1-3 (Jan. 21, 2010).

Somaxon Pharmaceuticals Provides Update on Preclinical and Clinical Programs for Silenor™, Somaxon Pharmaceuticals Press Release, San Diego, CA, p. 1-3 (Sep. 11, 2006).

Somaxon Pharmaceuticals Provides Update on Silenor® Development Program for the Treatment of Insomnia, Somaxon Pharmaeuticals, p. 1-5, (Jul. 19, 2006).

Somaxon Pharmaceuticals Provides Update on SILENOR™ Development Program, Somaxon Pharmaceuticals Press Release, San Diego, CA, p. 1-3 (May 9, 2007).

Somaxon Pharmaceuticals Provides Update on SILENOR™ Preclinical Program, Somaxon Pharmaceuticals Press Release, San Diego, CA, p. 1-7 (Feb. 13, 2007).

(56) References Cited

OTHER PUBLICATIONS

Somaxon Pharmaceuticals Receives Complete Response Letter from the FDA for Silenor® (Doxepin), Somaxon Pharmaceuticals Press Release, San Diego, CA, p. 1-3 (Feb. 26, 2009).
Somaxon Pharmaceuticals Receives Complete Response Letter from the FDA for Silenor® NOA, Somaxon Pharmaceuticals Press Release, San Diego, CA, p. 1-3 (Dec. 7, 2009).
Somaxon Pharmaceuticals Resubmits New Drug Application for Silenor® (Doxepin) for the Treatment of Insomnia, Somaxon Pharmaceuticals Press Release, San Diego, CA, p. 1-4 (Jun. 4, 2009).
Somaxon Pharmaceuticals Scheduled to Meet with FDA to Discuss Complete Response Letter for Silenor® NOA, Somaxon Pharmaceuticals Press Release, San Diego, CA (Dec. 17, 2009).
Somaxon Pharmaceuticals' Silenor® Data Presented at the 22nd Annual Meeting of the Associated Professional Sleep Societies, Somaxon Pharmaceuticals Press Release, San Diego, CA, p. 1-4 (Jun. 12, 2008).
Somaxon Pharmaceuticals' Silenor™ Demonstrates Positive Results in a Phase 3 Transient Insomnia Clinical Trial, Somaxon Pharmaceuticals, p. 1-5, (Oct. 23, 2006).
Somaxon Pharmaceuticals' Silenor™ Demonstrates Positive Results in its Third Phase 3 Clinical Trial in Insomnia, Somaxon Pharmaceuticals, p. 1-6, (Nov. 20, 2006).
Somaxon Pharmaceuticals Submits New Drug Application for Silenor™ for the Treatment of Insomnia, Somaxon Pharmaceuticals Press Release, San Diego, CA, p. 1-6 (Jan. 31, 2008).
Somaxon Pharmaceuticals to Present Data at the 22nd Annual Meeting of the Associated Professional Sleep Societies, Somaxon Pharmaceuticals Press Release, San Diego, CA (Jun. 4, 2008).
Somaxon Pharmaceuticals, Inc. Initiates Phase III Clinical Trials of Silenor™ in Patients with Insomnia, Somaxon Pharmaceuticals Press Release, San Diego, CA, p. 1-3 (Jun. 9, 2005).
Somaxon Pharmaceuticals, Inc. Initiates Second Phase III Clinical Trials of Silenor™, Somaxon Pharmaceuticals Press Release, San Diego, CA (Sep. 20, 2005).
Somaxon Pharmaceuticals Announces the Completion of Enrollment in a Phase II Study 291 Evaluating S0-101 for Ihe Treatment of Sleep Maintenance Insomnia in Adults, Somaxon Pharmaceuticals, p. 1, (Oct. 7, 2004).
Somaxon's Silenor™ Demonstrates Positive Results in Long-Term Phase 3 Clinical Trial in Elderly Patients with Insomnia, Somaxon Pharmaceuticals, p. 1-7, (Dec. 18, 2006).
Sominex Caplets. Nightime sleep-aid—Diphenhydramine. GlaxoSmithKline. Consumer Healthcare, L.P. Label 3 pages.
Sonata (Zaleplon) Capsules. Prescribing Information. King Pharmaceuticals. Feb. 2009. p. 1-15.
Anocili-Isreal , et al., "Identification and Treatment of Sleep Problems in the Elderly Review Article", Sleep Medicine Reviews 1(1), 1997, 3-17.
Chen , Sleep, Depression and Antidepressants, British Journal of Psychiatry, 135: 385-402, (1979).
Haritos , et al., Stereoselective measurement of E- and Z-doxepin and its N-desmethyl and hydroxylated metabolites by gas chromatography-mass spectrometry. J Chromatogr B Biomed Sci Appl. 736(1-2):201-8 (1999).
Krakowski , Seminar on Psychopharmacology—Auspices of Academy of Psychosomatic Medicine, Dec. 8-9, 1968 Freeport, Grand Bahama Island, Psychosomatics, pp. 7-63 (1968).
Neubauer , Sleep Problems in the Elderly. Am Fam Physician. 59(9): 2551-2558 (May 1999).
Phillips , et al., Sleep Disorders in the Elderly, Sleep Medicine 2: 99-114 (2001).
Schweitzer , et al., Sleepiness and Performance During Three-Day Administration of Cetirizine or Diphenhydramine. J Allergy Clin Immunol. 94(4): 716-724 (1994).
Sokoliess , et al., Separation of (Z)- and (E)-isomers of thioxanthene and dibenz[b,e]oxepin derivatives with aalixarenes and resorcinarenes as additives in nonaqueous capillary electrophoresis. Electrophoresis. 24(10):1648-57 (2003).
Yan , et al., Stereoselective and simultaneous measurement of cis- and trans-isomers of 314 doxepin and N-desmethyldoxepin in plasma or urine by high-performance liquid chromatography. J Chromatogr B Biomed Sci Appl. 691(1):131-8 (1997).
Yan , et al., Stereoselective in vivo and in vitro studies on the metabolism of doxepin and Ndesmethyldoxepin. Xenobiotica. 27(12): 1245-1257 (1997).
Electronic File History of U.S. Appl. No. 11/804,722, filed May 18, 2007 (Abandoned) containing Office Action(s) dated Jun. 15, 2010, Nov. 8, 2010 and Jun. 2, 2011 and Applicant Response(s) filed Oct. 15, 2010.
Electronic File History of U.S. Appl. No. 11/867,595, filed Oct. 4, 2007 containing Office Action(s) dated Oct. 21, 2010, and May 10, 2011 and Applicants Response(s) filed Apr. 20, 2011, Sep. 30, 2011, Nov. 10, 2011 and Jul. 11, 2012 as of Sep. 26, 2012.
Electronic File History of U.S. Appl. No. 12/022,628, filed Jan. 30, 2008 containing Office Action(s) dated Mar. 6, 2009 and Nov. 20, 2009—abandoned.
Electronic File History of U.S. Appl. No. 12/022,788, filed Jan. 30, 2008 containing Office Action(s) dated Mar. 9, 2009 and Dec. 9, 2009—abandoned.
Electronic File History of U.S. Appl. No. 12/102,985, filed May 6, 2011 (Abandoned) containing Office Action(s) dated Mar. 16, 2012 and Applicant(s) submissions Dec. 22, 2011 and Sep. 17, 2012 abandoned.
Electronic File History of U.S. Appl. No. 12/301,457, filed Apr. 12, 2010 containing Office Action(s) dated Jun. 7, 2012 and Applicants Response(s) filed Apr. 12, 2010 and Nov. 29, 2012 as of Dec. 17, 2012.
Electronic File History of U.S. Appl. No. 12/976,866, filed Dec. 27, 2010 (Abandoned) containing Office Action(s) dated Oct. 19, 2011 and Dec. 8, 2011 and Applicants Response filed Sep. 30, 2011.
German Federal Gazette (BAnz) No. 240 of Dec. 22, 1992, p. 9545 (vol. 44).
Guidance for Industry SUPAC-IR/MR: Immediate Release and Modified Release Solid Oral Dosage Forms—Manufacturing Equipment Addendum, Jan. 1999.
International Preliminary Report on Patentability & Written Opinion dated Apr. 7, 2009 in PCT/US2007/080492, filed Oct. 4, 2007.
International Preliminary Report on Patentability & Written Opinion dated Jan. 20, 2009 in PCT/US2007/016464, filed Jul. 20, 2007.
International Preliminary Report on Patentability & Written Opinion dated Nov. 21, 2008 in PCT/US2007/012105, filed May 18, 2007.
International Preliminary Report on Patentability & Written Opinion dated Nov. 21, 2008 in PCT/US2007/012106, filed May 18, 2007.
International Preliminary Report on Patentability & Written Opinion dated Nov. 21, 2008 in PCT/US2007/012107, filed May 18, 2007.
International Preliminary Report on Patentability and Written Opinion dated Jun. 18, 2009 in PCT/US2007/086682, filed Dec. 6, 2007.
International Preliminary Report on Patentability dated Dec. 4, 2008 in PCT/US2007/011893, filed May 18, 2007.
International Preliminary Report on Patentability dated May 7, 2009 in PCT/US2007/082569, filed Oct. 25, 2007.
International Preliminary Report on Patentability dated Oct. 13, 2009 in PCT/US2008/060131, filed Apr. 11, 2008.
International Search Report and Written Opinion dated Aug. 13, 2009 in PCT/US2009/042912, filed May 5, 2009.
International Search Report and Written Opinion dated Jan. 19, 2008 in PCT/US2008/060131, filed Apr. 11, 2008.
International Search Report and Written Opinion dated Jan. 21, 2008 in PCT/US2007/012107, filed May 18, 2007.
International Search Report and Written Opinion dated Jul. 29, 2008 in PCT/US2007/086682, filed Dec. 6, 2007.
International Search Report dated Dec. 10, 2007 in PCT/US2007/016464, filed Jul. 20, 2007.
International Search Report dated Jan. 24, 2008 in PCT/US2007/012105, filed May 18, 2007.
International Search Report dated Jan. 24, 2008 in PCT/US2007/012106, filed May 18, 2007.

(56) References Cited

OTHER PUBLICATIONS

International Search Report dated Jun. 17, 2008 in PCT/US2007/080492, filed Oct. 4, 2007.
International Search Report dated Mar. 18, 2008 in PCT/US2007/082569, filed Oct. 25, 2007.
Lunesta (Eszopiclone) Tablets 1 mg, 2 mg, 3 mg. Prescribing Information. Package Insert. Sepracor Inc. Jan. 2009. p. 1-2.
National Academy of Sciences, Sleeping Pills, Insomnia, and Medical Practice, Institute of Medicine, 32-33,103,125,149,169,198, (1979).
Natrol Melatonin 3 mg. 60 Tablets. Dietary Supplement. Manufactured by Natrol, Inc. Label p. 1-3.
Charman, Lipids, Lipophilic Drugs, and Oral Drug Delivery—Some Emerging Concepts. J Pharm Sci .89(8):967-78 (2000).
Declerck, et al., Increase in Slow-wave Sleep in Humans with the Serotonin-S2 Antagonist Ritanserin. Curr Ther Res. 41(4):427-432 (1987).
Dilger, et al., High-performance liquid chromatographic determination of trans-doxepin and desmethyldoxepin. Arzneimittelforschung. 38(10): 1525-8 (1988).
Faulkner, et al., Multiple-dose doxepin kinetics in depressed patients. Clin Pharmacol Ther. 34(4):509-15 (1983).
Ghabrial, et al., Geometric isomerization of doxepin during its N-demethylation in humans. Drug Metab Dispos. 19 (3):596-9 (1991).
Hsu, et al., Low-Dose Doxepin in the treatment of primary insomnia, Sleep, 28: suppl, p. A50, (2005).
Jacobsen, Low-Dose Trazodone as a Hypnotic in Patients Treated with MAOIs and Other Psychotropics: A Pilot Study, Journal of Clinical Psychiatry, 51: 298-392 (1990).
Masaki, et al., Involvement of Hypothalamic Histamine H1 Receptor in the Regulation of Feeding Rhythm and Obesity, Diabetes 53(9): 2250-2260, (2004).
Narasimhachari, et al., N-Alkylation of Secondary Amine Tricyclic Antidepressants as a General Method for Their Quantitation by GC-MS-SIM Technique. Analytical Lett. 12(B1):77-88 (1979).
Nicholson, et al., Modulation of sleep by trimipramine in man, European Journal of Clinical Pharmacol, 37: 145-150, (1989).
Nierenberg, et al., Management of Monoamine Oxidase Inhibitor-Associated Insomnia with Trazodone, Journal of Clinical Psychopharmacol, vol. 9 No. 1, p. 42-45, (1989).
O'Brien, et al., GLC determination of doxepin plasma levels. J Pharm Sci. 65(7):1068-9 (1976).
Ookuma, et al., Evidence for Feeding Elicited Through Antihistaminergic Effects of Tricyclic Antidepressants in the Rat Hypothalamus. Psychopharmacology (Berl). 101 (4): 481-485, (1990).
Palvimaki, et al., Interactions of selective serotonin reuptake inhibitors with the serotonin 5-HT2C receptor. Phychopharmacology, 126(3): 234-240 (1996).
Pollack, Is Biotechnology Losing Its Nerve?, NY Times (Feb. 29, 2004), pp. 1-4.
Roth, et al., Efficacy and Safety of doxepin 1, 3, and 6mg in elderly adults with primary insomnia, Sleep (Rochester),29: suppl. S (2006).
Roth, et al., Efficacy and Safety of Zolpidem-MR: A Double-Blind, Placebo-Controlled Study in Adults with Primary Insomnia, Sleep Med. 7(5): 397-406 (2006).
Shu, et al., Identification of Phenolic Doxepin Glucuronides from Patient Urine and Rat Bile. Drug Metab Disp. 18(6): 1096-1099 (1990).
Stimmel, et al., Mirtazapine: An Antidepressant with Noradrenergic and Specific Serotonergic Effects Pharmacotherapy, (1997) 17(1): 10-21.
New Drug Application 16-798 for Sinequan approved in 1978 (includes evaluation of insomnia indication on pp. 46-47, 54, 57, 59.
NyQUIL Cold & Flu. Nightime Relief. Acetaminophen, Doxylamine, Dextromethorphan, Alcohyl 10%. 6 Fl Oz. Vicks Label. 2 pages.
Nytol Quickcaps with Diphenhydramine HCI. Nightime Sleep-Aid. 72 Caplets. Label. 4 pages.
Partial International Search Report dated Apr. 8, 2008 in PCT/US2007/082569, filed Oct. 25, 2007.
Patent Information Leaflet, Sinequan™ (doxepin), United Kingdom, p. 1-2 (2002).
Pfizer, Chemist Review of NOA 17-516, Division of Neurophamacological Drug Products, Chemists Review #3, (1973).
Pharmaca Fennica. Published by the Finnish Centre for Medicine Information (Laaketietokeskus); SR Doxal; (1992).
Pharmaca Fennica. Published by the Finnish Centre for Medicine Information (Laaketietokeskus); SR Doxal; 612-613 (1988).
Pharmaca Fennica. Published by the Finnish Centre for Medicine Information (Laaketietokeskus); SR Doxal; 714 (1991).
Pharmaca Fennica. Published by the Finnish Centre for Medicine Information (Laaketietokeskus); SR Doxal; 830 (1995).
Pharmaca Fennica. Published by the Finnish Centre for Medicine Information (Laaketietokeskus); Ye R Doxal; 534-535 (2000).
Pharmaca Fennica. Published by the Finnish Centre for Medicine Information (Laakevalmisteet); SR Sinequan; 845-846 (1993).
Pharmaca Fennica. Published by the Finnish Centre for Medicine Information (Laaketietokeskus); SR Doxal; 738 (1993).
Pharmassure. Standardized. Valerian. Herbal Supplement. Minimum 0.8% Valerenic 219 Acids (2mg). 250 mg. 60 Softgel Capsules. Distributed by PharmAssure, Inc. Label. p. 1-4.
Physician's Desk Reference, 1999 ed., Medical Economics Company, Montvale NJ pp. 539-541 (Trazadone).
Physician's Desk Reference, 2000 ed., Medical Economics Company, Montvale NJ pp. 2366-2367 (Doxepine HCI).
Physician's Desk Reference, 2000 ed., Medical Economics Company, Montvale NJ pp. 3323-3324 (Trimipramine maleate).
Physician's Desk Reference, 2000 ed., Medical Economics Company, Montvale NJ pp. 549-551 (Amitriptyline HCI).
Physicians Desk Reference, Litton Industries, p. 1211, 93, (1976).
Physicians' Desk Reference, p. 1310-1312, (1990).
Physicians' Desk Reference, p. 1849-1850, (1990).
Physicians' Desk Reference, p. 2434-2435, (1990).
Polish Drug Application for Sinequan 10 mg capsules. 01474/93. p. 1-4 with attached Annex in 4 pages.
Polish Drug Application for Sinequan 25 mg capsules. 01475/93. p. 1-4 with attached Annex in 4 pages.
Restoril—Temazepam capsule. Mallinckrodt Inc. Prescribing Information. Revised Mar. 2006. p. 1-8.
Rodenbeck et al., The sleep-improving effects of doxepin are paralleled by a normalized plasma cortisol secretion in primary insomnia, Psychopharma. 170(4): 423-428 (2003).
Rozerem (ramelteon) tablets. Highlights of Prescribing Information. Takeda Pharmaceuticals. Revised Oct. 2008. p. 1-6.
Electronic File History, of U.S. Appl. No. 12/446,914, filed May 27, 2010 containing Office Action(s) dated Aug. 5, 2011, Jan. 20, 2012, Feb. 17, 2012 and Sep. 5, 2012 and Applicants Response(s) filed May 27, 2010, Jan. 20, 2012, and Aug. 17, 2012 as of Sep. 25, 2012.
Electronic File History of U.S. Appl. No. 11/781,165, filed Jul. 20, 2007 (now U.S. Pat. No. 7,915,307,338 issued Mar. 29, 2011) containing, Office Action(s) dated Oct. 14, 2008, Jul. 7, 2009, Sep. 29, 2009, 2-part Apr. 6, 2010, Oct. 21, 2010 and Nov. 12, 2010 and Applicant Response(s) filed Apr. 14, 2009, document Dec. 4, 2009, Jul. 6, 2010 and Oct. 21, 2010 as of Sep. 14, 2012.
Silenor (doxepin) Drug Description, RX List, Apr. 2, 2010, 1 page.
Adamzyk, et al., Quantitative determination of E- and Z-doxepin and E- and Z-desmethyldoxepin by high-performance liquid chromatography. Ther Drug Monit. 17(4):371-6 (1995).
Baldrick, Pharmaceutical excipient development: the need for preclinical guidance. Regul Toxicol Pharmacol. 32 (2): 210-218 (2000).
Bogaert, et al., Plasma levels of the cis- and trans-isomers of doxepin and desmethyldoxepin after administration of doxepin to patients. Arzneimittelforschung. 31(1):113-5 (1981).
Brunswick, et al., Relationship between tricyclic antidepressant plasma levels and clinical response in patients treated with desipramine or doxepin. Acta Psychiatr Scand. 67(6):371-7 (1983).
Conn, et al., Pattern of Use of Antidepressants in Long-Tern Care Facilities for the Elderly, Journal of Geriatric Psychiatry and Neurology, vol. 5:4, p. 228-232, (1992).
Ereshefsky, et al., Pharmacokinetic factors affecting antidepressant drug clearance and clinical effect: evaluation of doxepin and imipramine—new data and review. Clin. Chem. 34(5):863-80 (1988).

(56) References Cited

OTHER PUBLICATIONS

Fawcett, et al., Review of the Results from Clinical Studies on the Efficacy, Safety and Tolerability of Mirtazapine for the Treatment of Patients with Major Depression J. Affective Disorders (1998) 51: 267-285.

Friedel, et al., Relationship of blood levels of sinequan to clinical effects in the treatment of depression in aged patients. In. Mendels J, editor, Amsterdam: Excerpta Medica. p. 51-53 (1975).

Georgotas, Response of Depressive Symptoms to Nortiptyline, Phenelzine and Placebo, Br. J. Psychiatry (1987) 151:102-106.

Grundstrom, et al., Sedative Properties of Doxepin in Comparison with Diazepam, Psychopharmacology, 54: 165-169 (1977).

Hajak, et al., Nocturnal Melatonin Secretion and Sleep after Doxepin Administration in Chronic Primary Insomnia, Pharmacopsychiatry 29: 187-192, (1996).

Haritos, et al., Role of cytochrome P450 2D6 (CYP2D6) in the stereospecific metabolism of E- and Z-doxepin. Pharmacogenentics. 10(7):591-603 (2000).

Higuchi, et al., Pro-Drugs as Novel Delivery Systems, A.C.S. Symposium Series, American Chemical Society; vol. 14, (1975)—Title Pages Only.

Ribbentrop, et al., Pharmacologic studies of doxepin, an antidepressive agent with centrally anticholinergic and sedative effects. Arzneimittelforschung. 15:863-68 (1965). Translation of Abstract only.

Rodenbeck, et al., "The sleep-improving effects of doxepin are paralleled by a normalized plasma cortisol secretion in primary insomnia", Psychopharma 170(4), 2003, 423-428.

Rosseel, et al., Quantitative GLC determination of cis- and trans-isomers of doxepin and desmethyldoxepin. J Pharm Sci. 67(6):802-5 (1978).

Roth, et al., Psychopharmacolodgy: The Effects of Doxepin HCI on Sleep and Depression, Journal of Clinical Psychiatry, 43:9, p. 366-368 (1982).

Wheatley, Prescribing Short-Acting Hypnosedatives: Current Recommendations from a Safety Perspective, Drug Safety 7(2):106-115 (1992).

BPAI decision issued Dec. 11, 2012 in U.S. Appl. No. 11/804,720, filed May 18, 2007.

Civil Docket of the U.S. District Court, District of Delaware, Case #1 :11-cv-00537-RGA-MPT, printed Dec. 21, 2012 Involving U.S. Pat. Nos. 6,211,229 and 7,915,307 of Somaxan Pharmaceuticals, Inc., pp. 1-5.

Council on Drugs, Evaluation of Doxepin Hydrochloride (Sinequan), JAMA, 215(12): 1967-68 (Mar. 22, 1971).

Badenhorst, et al., Determination of doxepin and desmethyldoxepin in human plasma using liquid chromatography-tandem mass spectrometry. J Chromatogr B Biomed Sci Appl. 742(1):91-8 (2000).

Biggs, et al., Dosage schedule and plasma levels of doxepin and desmethyldoxepin. J Clin Psychiatry. 39(10):740-2 (1978).

Brunello, et al., Effect of Some Tricyclic and Nontricyclic Antidepressants on [H]lmiipramine Binding and Serotonin Uptake in Rat Cerebral Cortex After Prolonaed Treatment. Fundam Clin Pharmacol., 1: 327-333 (1987).

Bundgaard, Ed. Design of Prodrugs: Bioreversible derivatives for various functional groups and chemical entities, Elsevier, Amsterdam (1985). Chapter 1. p. 1-92.

Deuschle, et al., Doxepin and its Metabolites in Plasma and Cerebrospinal Fluid in Depressed Patients, Psychopharmacology, 131 (1): 19-22, (1997).

Dunleavy, et al., Changes During Weeks in Effects of Tricyclic Drugs on the Human Sleeping Brain, British Journal of Psychiatry, 120: 663-672, (1972).

Erman, et al., Comparative Efficacy of Zolpidem and Temazepam in Transient Insomnia, Human Psychopharma Clin Exp., 16: 169-176 (2001).

Faulkner, et al., Comparative assays for doxepin and desmethyldoxepin using high-performance liquid chromatography and high-performance thin-layer chromatography. J Pharm Sci. 72(10):1165-7 (1983).

Fulton, et al., Assessment of the Antidepressant Activity of Dothiepin and its Metabolites by Preclinical Tests. J Affect Dis. 4: 261-269 (1982).

Green, Douglas O., Clinical importance of doxepin antidepressant plasma levels. J Clin Psychiatry. 39(5):481-2 (1978).

Hartmann, Peter M., Clinical Pharmacology—Miratzapine: A Newer Antidepressant, American Family Physician (1999) 1-5.

Heal, et al., Comparative Pharmacology of Dothiepin, its Metabolites, and other Antidepressant Drugs. Drug Dev Res. 27: 121-135 (1992).

Hobbs, Distribution and Metabolism of Doxepin, Biochem. Pharmacol., 18(8): 1941-1954, (1969).

Hrdina, et al., Cis- and trans-isomers of doxepin and desmethyldoxepin in the plasma of depressed patients treated with doxepin. Ther Drug Monit. 12(2):129-33 (1990).

Joyce, et al., Doxepin plasma concentrations in clinical practice. Could there be a pharmacokinetic explanation for low concentrations? Clin Pharmacokinet. 10(4):365-70 (1985).

Kales, et al., Effects of Sinequan on sleep of Insomniac Subjects, Sleep Study Abstracts, p. 93, (1972).

Kirchheiner, et al., Contributions of CYP2D6, CYP2C9 and CYP2C19 to the biotransformation of E- and Z-doxepin in healthy volunteers. Pharmacogenetics. 12(7):571-80 (2002).

Kline, et al., Doxepin and Desmethyldoxepin Serum Levels and Clinical Response. In: Gottschalk LA MM, editor. Pharmacokinetics of psychoactive drugs: blood levels and clinical response. New York: Spectrum Press. p. 221-28 (1976).

Laimer, et al., Effect of Mirtazapine Treatment on Body Composition and Metabolism, J Clin Psychiatry, 67(3): 421-524 (2006).

Lapp, Chronic Fatigue Syndrome is a Real Disease, North Carolina Family Physician, 43:1, (1992).

Leucht, et al., Doxepin plasma concentrations: is there really a therapeutic range? J Clin Psychopharmacol. 21 (4):432-9 (2001).

Linnoila, et al., Clomipramine and doxepin in depressive neurosis. Plasma levels and therapeutic response. Arch Gen Psychiatry. 37(11):1295-9 (1980).

Manning, et al., Central Nervous System Effects of Meclizine and Dimenhydrinate: Evidence of Acute Tolerance to Antihistamines. J. Clin. Psychiatry 32:996-1002 (1992).

Mealy, et al., "Drugs Under Development for the Treatment of Psyciatric Distorders", Drugs Fut. 31(3), 2006, 266-284.

Mercer, et al., Dietary Induced Anorexia: A Review of Involvement of the Histominergic System, J Am Coll Nutr., 15(3): 223-230, (1996).

Moody, et al., Biotransformation of Doxepin by Cunninghamella E/egans, Drug Metab Dispo., 27(10): 1157-1164, (1999).

Orthen-Gambill, Antihistaminic Drugs Increase Feeding, While Histidine Suppresses Feeding in Rats, Pharmacol Biochem Behav., 31(1): 81-86, (1988).

Orthen-Gambill, et al., Differential Effects of Psychotropic Drugs on Feeding in Rats: Is Histamine Blockade Involved? Pharmacol Biochem Behav., 36(4): 837-841 (1990).

Pinder, R. M., et al., "Doxepin Up-to-Date: A Review of its Pharmacological Properties and Therapeutic Efficacy with Particular Reference to Depression", Drugs 13, 1977, 161-218.

Powell, et al., Compendium of Excipients for Parenteral Formulations, PDA J Pharm Sci Technol. 52(2): 238-311 (1998).

Prakash, et al., Deuterium Labelling of the Antidepressant Drug Doxepin for Disposition Studies in Human Subjects. J Lab Comp Radiopharma. 28(9): 1037-47 (1990).

Roche, Bioreversible Carriers in Drug Design: Theory and Application, Pergamon Press: New York, pp. 14-21 (1987)—Contents Pages Only.

Roth, et al., Efficacy and Safety of Doxepin 1 mg, 3mg, and 6mg in Adults with Primary Insomnia, Sleep, 30(11): 1555-1561 (Nov. 2007).

Scharf, et al., Efficacy and Safety of Doxepin 1 mg, 3 mg, and 6 mg in Elderly Patients 249 With Primary Insomnia: A Randomized, Double-Blind, Placebo-Controlled Crossover Study. J Clin Psychiatry 69(10): 1557-1564 (Oct. 2008).

Seifritz, E, Contribution of Sleep Physiology to Depressive Pathophysiology, Neuropsychopharmacology 25(5) S1: S85-S88 (Nov. 2001).

(56) References Cited

OTHER PUBLICATIONS

Stella, et al., "Prodrugs: Challenges and Rewards Part 1", Biotechnology: Pharmaceutical Aspects, 2007, p. 24.
Ward, et al., Doxepin plasma levels and therapeutic response in depression: preliminary findings. J Clin Psychopharmacol. 2(2):126-8 (1982).
Wyatt, et al., Carbon13 NMR OF Z- and E-Doxepin Hydrochloride. Applied Spectroscopy. 49(4):538-542 (1986).
Ziegler, et al., Doxepin kinetics. Clin Pharmacol Ther. 23(5):573-9 (1978).
Zung, Effect of Antidepressant Drugs on Sleeping and Dreaming, Excerpta Medica Foundation International Congress Series, No. 150, 1824-1826, (1968).
Summary Basis for approval of Adapin (1972) Pursuant to FOIA Request filed in 1981.
Summary Basis for approval of Sinequan® (1973) Pursuant to FOIA Request filed in 1973 (sedative, tranquilizer and sleep effects mentioned for example on pp. 50, 54-56, 58-59).
Technical Information/Summary of Drug Characteristics (SPC), Pfizer, p. 1-4, (2004).
Tylenol PM Extra Strength Pain Reliever. Nighttime Sleep Aid. Contains Acetaminophen, Diphenhydramine HCI. 24 Geltabs. Label. 4 pages.
Tylenol PM. Extra Strength Pain Reliever. Nighttime Sleep Aid. Contains Acetaminophen, Diphenhydramine HCI. 50 Caplets. Label. 4 pages.
Virtanen et al., Radioimmunoassay for doxepin and desmethyldoxepin., Acta Pharmacol Toxicol (Copenh). 47 (4):274-8 (1980).
Anon, "Quitaxon 10 mg cp pellic sec. Online", XP002507206, retrieved from the Internet: URL: <http://www.vidal.fr/medicament/wuitaxon-14133.htm> on Dec. 8, 2008.
Desyrel, trazadone hydrochloride tablet. Bristol-Myers Squibb Company. Prescribing Information. Revised Feb. 2009. p. 1-9.
Ebert, et al., Treating insomnia: Current and investigational pharmacological approaches. Pharmacol Thera., 112(3):612-629 (Mar. 2006).
Fava, Weight Gain and Antidepressants. J Clin Psychiatry (61 Suppl) 11: 37-41 (2000).
Gillin, et al., Successful Separation of Depressed, Normal, and Insomniac Subjects by EEG Sleep Data, Arch Gen Psychiatry, vol. 36, p. 85-90, (1979).
Halcion, Triazolam tablet. Pharmacia and Upjohn Company. Prescribing Information. Revised Jan. 2009. p. 1-10.
Hartmann, et al., The Effects of Long Term Administration of Psychotropic Drugs on Human Sleep: 111. The Effects of Amitriptyline, Psychopharmacologia, 33: 185-202 (1973).
Hartter, et al., The N-demethylation of the doxepin isomers is mainly catalyzed by the polymorphic CYP2C19. Pharm Res. 19(7):1034-7 (2002).
Hellberg, et al., The Hydrolysis of the Prostaglandin Analog Prodrug Bimatoprost to 17-Phenyl-Trinor PGF2 by Human and Rabbit Ocular Tissue. J Ocul Pharmacol Ther., 19(2): 97-103 (2003).
Hohagen, et al., Treatment of Primary Insomnia with Trimipramine: An Alternative to Benzodiazepine Hypnotics? Eur Arch Psychiatry Clin Neurosci. 244(2): 65-72 (1994).
Luo et al., The Quaternary Ammonium-Linked Glucuronide of Doxepin: A Major Metabolite in Depressed Patients treated with Doxepin. Drug Metab Dispos., 19(3): 722-724, (1991).
Masaki, et al., The Hypothalamic H1 Receptor: A Novel Therapeutic Target for Disrupting Diurnal Feeding Rhythm and Obesity. Trends Pharmacol Sci. 27(5): 279-284, (2006).
Midha, et al., Stereoselective pharmacokinetics of doxepin isomers. Eur J Clin Pharmacol. 42(5):539-44 (1992).
Newcomer, et al., The Metabolic Effects of Antipsychotic Medications, Can J Psychiatry. 51 (8): 480-491 (2006).
Pecknold, et al., Trimipramine, Anxiety, Depression and Sleep, Drugs, vol. 38: Suppl. 1, p. 25-31, (1989).
Pollack, et al., The Selective GABA Reuptake Inhibitor Tiagabine for the Treatment of Generalized Anxiety Disorder: Results of a Placebo-Controlled Study, J Clin Psychiatry 66:1401-1408 (Nov. 2005).
Richardson, et al., Tolerance to Daytime Sedative Effects of H1 Antihistamines. J Clin Psychopharmacol. 22(5): 511-515 (2002).
Richelson, Tricyclic Antidepressants and Histamine H1 Receptors, Mayo Clin Proc., 54:669-67 4, (1979).
Shu, et al., The Identification of Urinary Metabolites of Doxepin in Patients. Drug Metabolism & Disposition, Drug Metabolism & Disposition, 18(5): 735-741 (1990).
Vincent, et al., Use of Human Sleep as a Test of Drug's Psychotropic Action with Doxepin as an example, Bordeaux Medical, No. 10, 2650-51, 2653-54, 2657-57, and 2661, (1971).
Voshaar, et al., Zolpidem is not Superior to Temazepam with Respect to Rebound Insomnia: A Controlled Study. Eur Neuropsychopharmacol. 14(4): 301-306 (2004).
Ware, Tricyclic Antidepressants in the Treatment of Insomnia, Journal of Clinical Psychiatry, 44 [9, Section 2]: 25-28 (1983).
ABPI (Association of the British Pharmaceutical Industry) Compendium of Data Sheets & SmPC's, 1999-2000; Pfizer Limited, p. 1158.
ABPI (Association of the British Pharmaceutical Industry) Compendium of Data Sheets and Summaries of Product Characteristics, 1996-1997; Pfizer Limited, p. 751-752.
ABPI (Association of the British Pharmaceutical Industry) Data Sheet Compendium 1991-1992; Pfizer Limited, p. 1147-1149.
ABPI (Association of the British Pharmaceutical Industry) Data Sheet Compendium 1993-1994; Pfizer Limited, p. 1205-1207.
ABPI (Association of the British Pharmaceutical Industry) Data Sheet Compendium 1994-1995; Pfizer Limited, p. 1150-1151.
ABPI (Association of the British Pharmaceutical Industry) Data Sheet Compendium 1995-1996; Pfizer Limited, p. 1239-1240.
ABPI (Association of the British Pharmaceutical Industry) Data Sheet Compendium 1998-1999; Pfizer Limited, p. 970-971.
ABPI (Association of the British Pharmaceutical Industry) Medicines Compendium, 2002; Pfizer Limited, p. 1792-1793.
Ambien (Zolpidem Tartrate) tablets CIV. Highlights of Prescribing Information. Revised Jun. 2009. Sanofi-Aventis U.S. LLC. p. 1-18.
Ambien (Zolpidem Tartrate) tablets CIV. Prescribing Information. Revised Jun. 2008. Sanofi-Aventis U.S. LLC. p. 1-22.
Ambien CR (zolipidem tartrate extended-release). Highlights of Prescribing Information. Package Insert. Jan. 2008, Sanofi-Aventis U.S. LLC. p. 1-7.
Ancoli-Isreal, et al., Identification and Treatment of Sleep Problems in the Elderly, Review Article, Sleep Medicine Reviews, 1(1): 3-17 1997.
Electronic File History of U.S. Appl. No. 11/804,720, filed May 18, 2007 containing Office Action(s) dated Feb. 25, 2009, Nov. 30, 2009, Mar. 17, 2011, Jul. 27, 2011, and Aug. 16, 2011 and Applicant Response(s) filed Aug. 25, 2009, May 27, 2010, Dec. 27, 2010 and May 17, 2011.
Electronic File History of U.S. Appl. No. 12/101,917, , filed Apr. 11, 2008 containing Office Action(s) dated Oct. 21, 2010, May 10, 2011, Jan. 12, 2012 and Nov. 21, 2012 Applicants Response(s) filed Dec. 2, 2008, Dec. 29, 2011 and Jan. 30, 2012 as of Dec. 17, 2012.
Electronic File History of U.S. Appl. No. 13/007,334, filed Jan. 14, 2011 (Abandoned) containing Office Action(s) dated Apr. 17, 2012, as of Sep. 25, 2012.
Becker, et al., Pharmacologic and Nonpharmacologic Treatments of Insomnia, Neurol Clin. 23: 1149-1163 (2005).
Burch, et al., Amitriptyline pharmacokinetics. A crossover study with single doses of amitriptyline and nortriptyline, Psychopharmacology (Berl), 1981; 74(1):35-42.
Dugovic, et al., 5-HT2 Receptors could be Primarily Involved in the Regulation of Slowwave Sleep in the Rat. Euro J Pharma., 137: 145-146 (1987).
Elavil, Amitriptyline Hydrochloride—amitriptyline hydrochloride tablet, film coated. Mutual Pharmceutical Company, Inc. Revised Sep. 2007. p. 1-9.
Hrdina, et al., Antidepressant plasma levels and clinical response in depressed patients treated with oxaprotiline and doxepin. Int Clin Psychopharmacol. Jul;3(3):205-14 (1988).

(56) References Cited

OTHER PUBLICATIONS

Luchtefeld, Answers to the Most Common Questions Regarding Prescription Drugs—Safeguard Your Health, Jenry Consulting 1999, Retrieved from the Internet: <http://www.grandtimes.com/Answer Drugs.html> p. 1-3.
Mayers, et al., Antidepressants and their effect on sleep, Hum Psychopharmacol., 20(8):533-559 (Dec. 2005).
Remington, "The Science and Practice of Pharmacy", 21st Ed. Lippincott Williams and Wilkins. Table of Contents Only, 2006.
Richelson, et al., Antagonism by Antidepressants of Neurotransmitter Receptors of Normal Human Brain in Vitro, J Pharmacol Exp Ther. 230(1): 94-102 (1984).
Schatzberg, et al., "Hypnotics" Manual of Clinical Psychopharmacology, American Psychiatric Press, Inc., Washington D.C., p. 173-189, (1986).
Thase, Michael E., Antidepressant Treatment of the Depressed Patient with Insomnia, J. Clin. Psychiatry (1999) 60 (Suppl. 17): 28-31.
Wolfe, Antidepressant Withdrawal Reactions. Am Fam Physician. 56(2): 455-462, (1997).
Zimmermann, et al., "Epidemiology, implications and mechanisms underlying drug-induced weight gain in psychiatric patients" J. Psychiatric Research (2003) 37: 193-220.
Adapin, (Doxepin, Sinequan) drug side effects. depression-guide. com, [online] 2005 [retrieved on Sep. 15, 2010]. Retrieved from the internet: <URL: http://www.depression-guide.com/adapin.htm> 3 pages.
Albemarle Pulmonary Medicine Associates, 2000 [online]. [retrieved on ]. Retrieved from the Internet: <URL: http://apma-nc.com/PatientEducation/INSOMNIA.HTM> p. 104.
Ambien CR (zolpidem tartrate extended release) Healthcare Professional Information. [online] "Healthcare Professionals. Help your insomnia patients meet the day on." [retrieved on Jul. 6, 2010]. Retrieved from the internet: <URL: http://www.ambiencr.com/hcp/zolpidem-tartrate.aspx> pp. 1-2.
Anon, Quitaxon 10 mg cp pellic sec., [online] 2006 [retrieved on Jan. 25, 2012]. Retrieved from the Internet: <URL : http://www.vidal.fr/Medicament/quitaxon-14133.htm>.
CBS.com, "Ambien May Prompt Sleep-Eating" [online] [retrieved on Mar. 15, 2006]. Retrieved from the Internet: <URL: http://www.cbsnews.com/stories/2006/03/15/earlyshow/health/> 2 pages.
Chloral Hydrate Drug Information, Professional Drugs.com [online] [retrieved on Jul. 6, 2010]. Retrieved from he Internet: <URL: http://www.drugs.com/mmx/chloral-hydrate.html> pp. 1-15.
Doxal. Laakeopas. [online] [retrieved on Nov. 28, 2005]. Retrieved from the Internet: <URL: http://www.coronaria.fi/www/mtv3/laakkeet.php?id=299>.
Doxal. Laakkeet. [online] [retrieved on Nov. 28, 2005]. Retrieved from the Internet: <URL: http:www.tohtori.fi/laakkeet/tuote.php3?10=412>.
Doxepin. Find Treatment & Support. The most reliable cancer treatment information. Cancer.org. [online] [retrieved on Jul. 6, 2010]. Retrieved from the Internet: <URL: http://www.cancer.org/docroot/CDG/content/CDG_doxepin.asp?internal=1> pp. 1-6.
NyQuil Oral, Drugs & Medications. WebMD [online] [retrieved on Jul. 6, 2010]. Retrieved from the Internet: <URL: http://www.webmd.com/drugs/drug-6104-NyQuil+Oral.aspx?drugid=6104&drugname=NyQuil+Oral&source=1> pp. 1-3.
Nytol Oral, Drugs & Medications. WebMD [online] [retrieved on Jul. 6, 2010]. Retrieved from the Internet: <URL: http://www.webmd.com/drugs/drug-10538-Nytol+Oral.aspx?drugid=10538&drugname=Nytrol+Oral&source=0> pp. 1-2.
Sinequan (Doxepin, Adapin): A guide to sinequan side effects. depression-guide.com [online], 2005 [retrieved on Jul. 6, 2010]. Retrieved from the Internet: <URL: http://www.depression-guide.com/sinequan.htm> pp. 1-3.
Sinequan Dosage. eMEDTV Clinaero, Inc. [online] [retrieved on Jul. 6, 2010]. Retrieved from the Internet: <URL: http://depression.emedtv.com/sinequan/sinequan-dosage.html> pp. 1-2.
Sominex Oral. Drugs & Medications. WebMD [onlilne] [retrieved on Jul. 6, 2010] Retrieved from the Internet: <URL: http://www.webmd.com/drugs/drug-15470-Sominex+Oral.aspx?drugid=15470&drugname=Sominex+Oral&source=1> pp. 1-3.
Sonata Official FDA information, side effects and uses. Drug Information Online, Drugs.com [onlilne] [retrieved on Jul. 6, 2010] Retrieved from the Internet: <URL: http://www.drugs.com/pro/sonata.html> pp. 1-22.
Tylenol PM Oral. Drugs & Medications. WebMD [online] [retrieved on Jul. 6, 2010]. Retrieved from the Internet: <URL: http://www.webmd.com/drugs/drug-74986-Tylenol+PM+Oral.aspx?drugid=74986&drugname=Tylenol+PM+Oral&source=1> pp. 1-3.
Zaleplon Capsules: Drug Information Online. Drugs.com [online] [retrieved on Aug. 25, 2009]. Retrieved from the Internet: <URL: http://www.drugs.com/pro/zaleplon.html?printable=1> pp. 1-23.
Approval data of the German drug regulatory authorities. DIMDI: AMIS—Public Part (AJ29).German Institute of Medical Documentation and Information within the scope of the Federal Ministry of Health. Pfizer Pharma GmBH. Sinquan 10 mg; capsules, Sinquan 100; capsules; Sinquan 100 mg; capsules, Sinquan 25 Intramuscular; solution; Sinquan 25 mg; capsules, Sinquan 50 mg; capsules, Sinquan 75 mg; capsules. [retrieved Nov. 16, 2005] Retrieved from the Internet: <https://gripsdb.dimdi.de/session/0511161521292992047/13docs.htm.>.
Saul, Stephanie, "Study Links Ambien Use to Unconscious Food Forays", The New York Times [online] [retrieved Mar. 14, 2006]. Retrieved from the Internet: <http://www.nytimes.com/2006/03/14/health/14sleep.html>, 4 pages.
Ambien CR (zolpidem tartrate extended release) tablets-CIV. Full Prescribing Information. Sep. 2009. [retrieved Jul. 6, 2010] Retrieved from the internet: <http://products.sanofiaventis.us/ambien cr/ambiencr.html.> p. 1-32.
Haute Autorite De Sante (France): Avis Dec. 13, 2006 [Online] 2006, XP002507207; [retrieved on Dec. 8, 2008] Retrieved from the Internet: <URL:http://www.hassante.fr/portail/icms/c 475580/quitaxon>.
U.S. Appl. No. 16/207,584; Dubé et al.; filed Dec. 3, 2018.
Preliminary Amendment for U.S. Appl. No. 16/207,584, filed Dec. 3, 2018.

ULTRA LOW DOSE DOXEPIN AND METHODS OF USING THE SAME TO TREAT SLEEP DISORDERS

CROSS-REFERENCE TO RELATED APPLICATIONS

This application is a continuation of U.S. application Ser. No. 14/045,645, filed Oct. 3, 2013, which is a continuation of U.S. application Ser. No. 12/446,914, filed May 27, 2010, which is a National Stage of International Application No. PCT/US07/082569 filed Oct. 25, 2007 which claims the benefit of U.S. Provisional Application No. 60/854,399 filed on Oct. 25, 2006 entitled ULTRA LOW DOSE DOXEPIN AND METHODS OF USING THE SAME TO TREAT SLEEP DISORDERS; U.S. Provisional Application No. 60/873,056, filed on Dec. 6, 2006, entitled COMBINATION THERAPY USING LOW-DOSE DOXEPIN FOR THE IMPROVEMENT OF SLEEP; and U.S. Provisional Application No. 60/910,586, filed on Apr. 6, 2007, entitled COMBINATION THERAPY USING LOW-DOSE DOXEPIN FOR THE IMPROVEMENT OF SLEEP; each of which applications is incorporated herein by reference in its entirety.

BACKGROUND OF THE INVENTION

Field of the Invention

The invention relates to ultra low doses of doxepin, as well as pharmaceutically acceptable salts and prodrugs of the same; compositions containing the same, and the use of any of the aforementioned for the treatment of sleep disorders.

Description of the Related Art

Sleep is essential for health and quality of life. Insomnia is a subjective complaint of dissatisfaction with the quantity, quality or timing of sleep. Insomnia is estimated to occur in approximately 12% to 25% of the general population, although this is probably an underestimate as there is evidence that many adults do not report their sleep problems to a health care professional.

One study has found that fewer than 15% of those who suffer from insomnia are treated with prescription medications. Medications commonly used to treat insomnia include sedative antidepressants, antihistamines, benzodiazepines, and non-benzodiazepine hypnotics. Various side effects are associated with the commonly used medications. For example, a side effect of some hypnotics is to reduce slow wave sleep. Other side effects of concern are possible daytime residual effects related to sedation, rebound insomnia, and minor side effects specific to each drug class. Tolerance to beneficial effects on sleep is thought to occur with antihistamines and benzodiazepine and non-benzodiazepine hypnotics.

Until the arrival of the non-benzodiazepine hypnotics in the mid '90's, benzodiazepines were the most common drugs used for the pharmacological management of insomnia. These drugs work by binding to and activating sites on the GABA-A receptor complex. Short, intermediate and long-acting benzodiazepines such as triazolam, temazepam and flurazepam were all commonly prescribed for this indication. While these agents have proven to be efficacious and relatively safe, benzodiazepines are associated with a multitude of adverse effects, including residual daytime sedation ("hangover"), amnesia, memory loss and respiratory depression. Rebound insomnia, has also been associated with benzodiazepines. Tolerance to the hypnotic effects of the benzodiazepines is common and abrupt discontinuation can result in withdrawal symptoms such as agitation, perceptual changes, confusion, disorientation and insomnia.

Most recently non-benzodiazepine hypnotics have become the primary class of medications for the treatment of insomnia. The leading approved non-benzodiazepine insomnia medications, eszopiclone, zolpidem, and zaleplon, also work by binding to and activating the GABA-A receptors, but they are more selective in their binding than the benzodiazepines. All these drugs approved for the treatment of insomnia that act via the GABA-A receptor, including benzodiazepine and non-benzodiazepine hypnotics, have a potential for addiction and abuse and are classified as Schedule IV controlled substances by the U.S. Drug Enforcement Administration. As a result, many physicians are reluctant to prescribe, and patients are reluctant to take, these drugs for chronic use in treating insomnia. The prescribing of a Schedule IV controlled substance brings scrutiny from the Drug Enforcement Administration and other regulatory bodies, and requires registration and administrative controls in physicians' offices. Therefore, it is desirable to have a pharmacological agent for the treatment of insomnia which is more effective and/or has fewer side effects that those currently used.

Recently a new hypnotic with a mode of action different from other hypnotics has been introduced. Ramelteon is a melatonin receptor agonist with high affinity for melatonin MT1 and MT2 receptors. It is indicated for sleep onset insomnia but it has not been shown to produce a sleep maintenance benefit. It does not affect the GABA-A receptor complex, is not addicting and is not scheduled.

The sedative antidepressants account for a large percentage of the total prescriptions written for insomnia. The National Disease and Therapeutic index estimates that more than 60% of the 13 million annual trazodone prescriptions are written for the treatment of insomnia, even though trazodone is not indicated for that usage and has never been promoted for that condition. Even though there are very limited data to support the use of trazodone for insomnia and it is associated with undesirable side effects, trazodone is often prescribed because it is a non-scheduled agent, meaning non-addictive, unlike the benzodiazepines and other GABA-receptor agonists which are approved for the treatment of insomnia.

SUMMARY OF THE INVENTION

Some embodiments relate to methods for treating insomnia. In some embodiments, the methods for treating insomnia can include administering to a patient doxepin, a pharmaceutically acceptable salt thereof, or a prodrug thereof in a daily dosage ranging from about 0.0001 to about 0.49 milligrams. In some embodiments, the pharmaceutically acceptable salt of doxepin can be the hydrochloride salt thereof. In some embodiments, the prodrug of doxepin can be a prodrug ester. In some embodiments, the daily dosage can be about 0.001 to about 0.1 milligrams. In some embodiments, the daily dosage can be about 0.01 to about 0.099 milligrams. In some embodiments, the methods can be for treating a chronic insomnia or a non-chronic insomnia. In some embodiments, the non-chronic insomnia can be a transient or a short term insomnia. In some embodiments, the insomnia can be onset insomnia or maintenance insomnia. In some embodiments, the methods can be used where the patient is not suffering from depression. In some embodiments, the methods can be used where the patient is suffering from depression. In some embodiments, the methods for treating insomnia can further include administering at least one of ramelteon, eszopiclone, zolpidem tartrate, or zaleplon. In some embodiments, the methods can further include administering at least one additional sleep medication. In some embodiments, the at least one additional sleep medication can be a 5-HT2 antagonist, ketanserin, a H3 agonist, an orexin antagonist, a noradrenergic antagonist, a galanin agonist, a CRH antagonist, Gaboxadol, other GABA-A direct antagonists, a GABA reuptake inhibitor, tiagabine, a growth hormone, a growth hormone agonist, estrogen, an estrogen agonist, or a melatonin agonist. Other examples of medications and substances that can be used in combination with ultra low doses as described herein can be found in U.S. Provisional Application No. 60/873,056, filed on Dec. 6, 2006, entitled COMBINATION THERAPY USING LOW-DOSE DOXEPIN FOR THE IMPROVEMENT OF SLEEP; and U.S. Provisional Application No. 60/910,586, filed on Apr. 6, 2007, entitled COMBINATION THERAPY USING LOW-DOSE DOXEPIN FOR THE IMPROVEMENT OF SLEEP; each of which applications is incorporated herein by reference in its entirety.

Other embodiments relate to compositions including doxepin, a pharmaceutically acceptable salt thereof, or a prodrug of doxepin. In some embodiments, the compositions can include doxepin, a pharmaceutically acceptable salt thereof, or a prodrug of doxepin in a dosage of about 0.0001 milligrams to about 0.49 milligrams. In some embodiments, the compositions further include a pharmaceutically acceptable carrier. In some embodiments, the pharmaceutically acceptable salt of doxepin can be the hydrochloride salt thereof. In some embodiments, the prodrug can be an ester. In some embodiments, the compositions can be in a form suitable for oral or nasal administration. In some embodiments, the compositions further include at least one of ramelteon, eszopiclone, zolpidem tartrate, or zaleplon. In some embodiments, the compositions further include at least one additional sleep medication. In some embodiments, the at least one additional sleep medication can be a 5-HT2 antagonist, ketanserin, a H3 agonist, an orexin antagonist, a noradrenergic antagonist, a galanin agonist, a CRH antagonist, Gaboxadol, other GABA-A direct antagonists, a GABA reuptake inhibitor, tiagabine, a growth hormone, a growth hormone agonist, estrogen, an estrogen agonist, or a melatonin agonist. Other examples of medications and substances that can be used in combination with ultra low doses as described herein can be found in U.S. Provisional Application No. 60/873,056, tiled on Dec. 6, 2006, entitled COMBINATION THERAPY USING LOW-DOSE DOXEPIN FOR THE IMPROVEMENT OF SLEEP; and U.S. Provisional Application No. 60/910,586, filed on Apr. 6, 2007, entitled COMBINATION THERAPY USING LOW-DOSE DOXEPIN FOR THE IMPROVEMENT OF SLEEP; each of which applications is incorporated herein by reference in its entirety.

Other embodiments relate to methods of shortening the time required to achieve a maximum plasma concentration of doxepin in a patient receiving doxepin therapy. In some embodiments, the methods of shortening the time required to achieve a maximum plasma concentration of doxepin in a patient receiving doxepin therapy includes administering to the patient about 0.0001 milligrams to about 0.49 milligrams of doxepin in a pharmaceutical composition without food.

Other embodiments relate to methods of shortening the time required to achieve sleep onset. In some embodiments, the methods of shortening the time required to achieve sleep onset include administering to the patient about 0.0001 milligrams to about 0.49 milligrams of doxepin in a pharmaceutical composition without food.

Other embodiments relate to methods of treating a sleep disorder. In some embodiments, the methods of treating a sleep disorder include providing a patient with about 0.0001 milligrams to about 0.49 milligrams of doxepin and providing the patient with instructions to take the doxepin without food.

Other embodiments relate to methods of increasing the oral bioavailability of doxepin. In some embodiments, the methods of increasing the oral bioavailability of doxepin include administering with food to a patient a pharmaceutical oral dosage form of doxepin in an amount of about 0.0001 milligrams to about 0.49 milligrams. In some embodiments, the methods of increasing the oral bioavailability of doxepin to a patient receiving doxepin therapy, include administering to the patient with food a pharmaceutical oral dosage form of doxepin comprising about 0.0001 milligrams to about 0.49 milligrams of doxepin, wherein the administration results in an $AUC_{0-\infty}$ that is greater than that achieved by the administration of the same amount of doxepin without food.

Other embodiments relate to methods of treating depression or anxiety. In some embodiments, the methods of treating depression or anxiety include administering about 0.0001 milligrams to about 0.49 milligrams of doxepin with food. In some embodiments, the methods of treating depression or anxiety, include providing a patient with doxepin in an amount of about 0.0001 milligrams to about 0.49 milligrams and providing the patient with instructions to take the doxepin with food. In some embodiments, the methods of treating depression or anxiety include providing a patient with doxepin in an amount of about 0.0001 milligrams to about 0.49 milligrams and providing the patient with information regarding a doxepin food effect.

Other embodiments relate to methods of decreasing the oral bioavailability of doxepin. In sonic embodiments, the methods of decreasing the oral bioavailability of doxepin include administering to a patient a pharmaceutical oral dosage form of doxepin comprising doxepin in an amount of about 0.0001 milligrams to about 0.49 milligrams without food. In some embodiments, the methods of decreasing the oral bioavailability of doxepin to a patient receiving doxepin therapy, include administering to the patient without food a pharmaceutical oral dosage form of doxepin including doxepin in an amount of about 0.0001 milligrams to about 0.49 milligrams, wherein the administration results in an $AUC_{0-\infty}$ that is less than that achieved by the administration of the same amount of doxepin with food.

Other embodiments relate to methods of alleviating a doxepin food effect. In some embodiments, the methods of alleviating a doxepin food effect include administering about 0.0001 milligrams to about 0.49 milligrams of doxepin to a patient in need thereof, wherein the patient is in a non-fasted state. In some embodiments, the methods of alleviating a doxepin food effect include administering about 0.0001 milligrams to about 0.49 milligrams of doxepin to a patient in need thereof, wherein the patient is in a fasted state.

Other embodiments relate to methods of minimizing side effects associated with a doxepin therapy. In some embodiments, the methods of minimizing side effects associated with a doxepin therapy include administering about 0.0001 milligrams to about 0.49 milligrams of doxepin to a patient with food.

Other embodiments relate to methods for improving the consistency of pharmacokinetics associated with doxepin therapy. In some embodiments of the methods for improving the consistency of pharmacokinetics associated with doxepin therapy, a patient receives multiple doxepin dosages over multiple days, comprising administering about 0.0001 milligrams to about 0.49 milligrams of doxepin to the patient in a fixed temporal relationship to food intake by the patient.

Other embodiments relate to products including doxepin. In some embodiments, the products include doxepin in an amount of about 0.0001 milligrams to about 0.49 milligrams and written instructions associated therewith to take the doxepin without food. In some embodiments, the products include doxepin in an amount of about 0.0001 milligrams to about 0.49 milligrams and written instructions associated therewith to take the doxepin with food. In some embodiments the products include doxepin in an amount of about 0.0001 milligrams to about 0.49 milligrams and written information associated therewith regarding a doxepin food effect.

DETAILED DESCRIPTION OF THE PREFERRED EMBODIMENT

Generally, embodiments of the present invention relate to ultra low doses of doxepin, pharmaceutically acceptable salts and prodrugs of doxepin, pharmaceutical compositions that include any the mentioned substances in ultra low doses, and use of the substances and compositions to treat an individual having a sleep disorder. For example, the sleep disorder can be insomnia. Also, some embodiments relate to methods of improving the pharmacokinetics of ultra low dose doxepin in a patient.

Surprisingly, the ultra low doses of doxepin, salts and prodrugs of the same are effective for treating sleep disorders. The ultra low doses of these substances have little or no abuse potential, have a rapid onset of action, and very minimal side effects. Prior to the present invention, very little was known about any sedative or hypnotic effects of ultra low doses of the aforementioned substances.

Some embodiments relate to methods for treating insomnia. The methods can include, for example, administering to a patient doxepin, a pharmaceutically acceptable salt thereof, or a prodrug thereof in an ultra low daily dosage. The dosage can be any ultra low dosage, for example, a dosage ranging from about 0.0001 to about 0.49 milligrams or any other described herein.

Still some embodiments relate to compositions. The compositions can include, for example, doxepin, a pharmaceutically acceptable salt thereof, or a prodrug of doxepin in an ultra low dosage. The dosage can be any ultra low dosage, including any described herein. For example, the dosage can be about 0.0001 milligrams to about 0.49 milligrams.

Also, some embodiments relate to methods of improving or manipulating the pharmacokinetics of doxepin, a salt or a prodrug thereof. The methods can include administering the particular substance (e.g., doxepin) with or without food, and including information regarding a food effect or instructions to take the doxepin with or without food, for example.

Compounds

Doxepin HCl is a tricyclic compound currently approved and available for treatment of depression and anxiety. Doxepin belongs to a class of psychotherapeutic agents known as dibenzoxepin tricyclic compounds, and is currently approved and prescribed for use as an antidepressant to treat depression and anxiety. Doxepin has a well-established safety profile, having been prescribed for over 35 years.

It is contemplated that doxepin for use in the methods described herein can be obtained from any suitable source or made by any suitable method. As mentioned, doxepin is approved and available in higher doses (75-300 milligrams) for the treatment of depression and anxiety. Doxepin HCl is available commercially and may be obtained in capsule form from a number of sources. Doxepin is marketed under the commercial name SINEQUAN® and in generic form, and can be obtained in the United States generally from pharmacies in capsule form in amounts of 10, 25, 50, 75, 100 and 150 mg dosage, and in liquid concentrate form at 10 mg/mL. Doxepin HCl can be obtained from Plantex Ltd. Chemical Industries (Hakadar Street, Industrial Zone, P.O. Box 160, Netanya 42101, Israel), Sifavitor S.p.A. (Via Livelli 1—Frazione, Mairano, Italy), or from Dipharma S.p.A. (20021 Baranzate di Bollate, Milano, Italy). Also, doxepin is commercially available from PharmacyRx (NZ) (2820 $1^{st}$ Avenue, Castlegar, B.C., Canada) in capsule form in amounts of 10, 25, 50, 75, 100 and 150 mg. Furthermore, Doxepin HCl is available in capsule form in amounts of 10, 25, 50, 75, 100 and 150 mg and in a 1.0 mg/ml liquid concentrate from CVS Online Pharmacy Store (CVS.com).

The recommended daily dose for the treatment of depression or anxiety ranges from 75 milligrams to 300 milligrams. Also, U.S. Pat. Nos. 5,502,047 and 6,211,229, the entire contents of which are incorporated herein by reference, describe the use of doxepin for the treatment chronic and non-chronic (e.g., transient/short term) insomnias at dosages below those used to treat depression. Doxepin can be obtained from any suitable source or prepared according to any suitable method. For example, it can be prepared according to the method described in U.S. Pat. No. 3,438,981, which is incorporated herein by reference in its entirety. As another illustration, doxepin can be prepared as taught in U.S. Pat. No. 3,420,851, which is incorporated herein by reference in its entirety.

Pharmaceutically Acceptable Salts:

As mentioned above, the methods and other embodiments described herein can utilize any suitable pharmaceutically acceptable salt or prodrug of doxepin. Therefore, the substitution or use in combination of salts and prodrugs is specifically contemplated in the embodiments described herein. The pharmaceutically acceptable salts and prodrugs can be made by any suitable method. The acids that may be used to prepare pharmaceutically acceptable acid addition salts are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, dislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

Prodrugs:

The term "prodrug" refers to a chemical entity that is rapidly transformed in vivo to yield an active entity, such as by hydrolysis in blood or inside tissues, for example.

Examples of prodrug groups can be found in, for example, T. Higuchi and V. Stella, in "Prodrugs as Novel Delivery Systems," Vol. 14, A.C.S. Symposium Series, American Chemical Society (1975); H. Bundgaard, "Design of Prodrugs," Elsevier Science, 1985; and "Bioreversible Carriers in Drug Design: Theory and Application," edited by E. B. Roche, Pergamon Press: New York, 14-21 (1987), each of which is hereby incorporated by reference in its entirety.

Insomnia

As mentioned above, some embodiments relate to the use of ultra low doses of doxepin, pharmaceutically acceptable salts, and/or prodrugs in the treatment of chronic and non-chronic insomnia. Examples of non-chronic insomnia include, for example, transient insomnia and short-term insomnia. Transient insomnia is an insomnia that is present for about one to several days, and is less than one week in duration. Short term insomnia is insomnia of about one to three weeks or four weeks in duration. Chronic insomnia is typically accepted to involve episodes greater than three (3) or four (4) weeks in duration. It is well known that the sleep deprivation resulting from such insomnia adversely affects cognition, safety and quality of life.

Furthermore, for chronic (e.g., greater than 3-4 weeks) or non-chronic insomnias, a patient may suffer from difficulties in sleep onset, sleep maintenance (interruption of sleep during the night by periods of wakefulness), sleep duration, sleep efficiency, premature early-morning awakening, or a combination thereof. Also, the insomnia may be attributable to the concurrent use of other medication, for example.

The chronic or non-chronic insomnia can be a primary insomnia or an insomnia that is secondary or attributable to another condition, for example a disease such as depression or chronic fatigue syndrome. In some aspects, the patient can be one that is not suffering from an insomnia that is a component of a disease. In some aspects, the methods can specifically exclude a patient with a secondary insomnia, for example, a patient suffering from insomnia as a component of depression or chronic fatigue syndrome. Some embodiments relate to methods of treating individuals suffering from insomnia that is caused by injury or the use of a medication or other substance. Treating such patients can specifically be excluded from other methods of treatment.

As previously mentioned, the chronic or non-chronic insomnia can be a primary insomnia, that is, one that is not attributable to another mental disorder, a general medical condition, or a substance. In many cases, such conditions may be associated with a chronic insomnia and can include, but are not limited to, insomnia attributable to a diagnosable DSM-IV disorder, a disorder such as anxiety or depression, or a disturbance of the physiological sleep-wake system. The non-chronic or short duration insomnia (e.g., less than 3-4 weeks) can have intrinsic or extrinsic causes. For example, non-chronic sleep disorders can include, but are not limited to, environmental sleep disorders as defined by the International Classification of Sleep Disorders (ICSD) such as inadequate sleep hygiene, altitude insomnia or adjustment sleep disorder (e.g., bereavement). Also, short-term insomnia may also be caused by disturbances such as shift-work sleep disorder.

In some embodiments, an otherwise healthy individual can be treated for insomnia. For example, doxepin (or any of the other ultra low dose substances) can be used to treat an individual suffering from an insomnia that is not attributable to a medical, psychiatric, or environmental cause. In some embodiments, methods of treating otherwise healthy individual can be specifically excluded from the methods.

In some embodiments an individual having a secondary insomnia, for example, insomnia as a component of his/her depression or other illness, can be treated, while in others methods of treatment of such individuals can be specifically excluded. Also, in some embodiments, an individual suffering from insomnia as part of chronic fatigue syndrome can be treated, while in other embodiments such the treatment of such individuals is excluded. Some embodiments relate to methods of treating individuals suffering from insomnia that is caused by injury or the use of a medication or other substance. Treating such patients can specifically be excluded from other methods of treatment.

Also, some embodiments cart include the use of low doses of doxepin, prodrugs or salts of the same in combination with other insomnia or sleep medications. For example, the methods can include the use of one or more of ramelteon, eszopiclone, zolpidem tartrate, zalepton or the like. Further, the methods can include the use of one or more of 5-HT2 antagonists (such as ketanserin), H3 agonists, orexin antagonists, noradrenergic antagonists, galanin agonists, CRH antagonists, Gaboxadol, other GABA-A direct antagonists, GABA reuptake inhibitors (such as tiagabine), growth hormone and growth hormone agonists, estrogen and estrogen agonists, melatonin agonists or the like. Other examples of medications and substances that can be used in combination with ultra low doses as described herein can be found in U.S. Provisional Application No. 60/873,056, filed on Dec. 6, 2006, entitled COMBINATION THERAPY USING LOW-DOSE DOXEPIN FOR THE IMPROVEMENT OF SLEEP; and U.S. Provisional Application No. 60/910,586, filed on Apr. 6, 2007, entitled COMBINATION THERAPY USING LOW-DOSE DOXEPIN FOR THE IMPROVEMENT OF SLEEP; each of which applications is incorporated herein by reference in its entirety.

Food Effect

It also should be mentioned that food can have an effect on the pharmacokinetics of sleep medication. The term "food effect" refers to a somewhat unpredictable phenomenon that can influence the absorption of drugs from the gastrointestinal tract following oral administration. The food effect can be designated "negative" when absorption is decreased, or "positive" when absorption is increased and manifested as an increase in oral bioavailability (as reflected by total exposure, usually defined as AUC). Alternatively, food effects can refer to changes in maximum concentration ($C_{max}$), or the time to reach maximum concentration ($T_{max}$), independently of overall absorption. As a result, some drugs have to be taken in either fasted or fed conditions to achieve the optimum effect. For example, patients may be instructed to take a drug with a meal, before a meal (e.g., one hour before a meal), or after a meal (e.g., two hours after a meal). However, many drugs are unaffected by food, and thus, can be taken in a fasted or a fed condition.

Accordingly, some embodiments relate to methods of improving the pharmacokinetics of doxepin, as well as the salts and prodrugs of such substances in a patient. In particular, the time to reach maximum concentration, $T_{max}$, can be minimized by administering the drug without food. Also, the time to reach maximum concentration can be increased by administering the substance with food. In addition, in a different embodiment, the total effective amount of drug that the patient receives can be maximized by administering the substance with food, while in other embodiments the oral bioavailability can be decreased by administering the substance without food. Because plasma concentrations and half-lives are already known to vary from patient to patient, knowledge of the food effect for a substance can help patients and physicians to eliminate this additional source of dosing uncertainty, to improve safety and tolerability, and improve therapies that utilize doxepin, or salts/prodrugs of the same. For example, as described more fully elsewhere herein, depending on the effect desired, the particular ultra low dose substance, such as an ultra low dose of doxepin, can be taken with food; it can be taken after the patient has gone without food for a period of time; and/or it can be taken some period of time prior to consuming food.

In some aspects, information regarding a food effect can be given to a patient or included with the drug. For example, instructions may be provided to patients receiving doxepin therapy or health care professionals involved in treatment of those patients that the drug should be administered with food, or at least in relatively close proximity to eating food or eating a meal (for example, within one hour or less). By way of example, such instructions could be provided orally or in written form. Some exemplary written forms include a label associated with the drug, on the container for the drug, packaged with the drug, or separately given to the patient apart from the drug. The invention further includes a package of any of the ultra low dose substances described herein with such written instructions associated therewith.

As mentioned, the ultra low dose substance can be administered without food or in a fasted state. For example, doxepin, prodrug, or salt can be administered at least about 30 minutes to about 6 hours after consuming food. More preferably, the substance can be taken at least about 1 hour to about 6 hours after consuming food. In some aspects the substance can be taken at least about 1, 2, 3, 4, 5 6 or more hours after consuming food.

Also, the ultra low dose substance can be administered at least about 30 minutes to about 6 hours before consuming any food, or more preferably, at least about 1 hour to about 3 hours before consuming food. In some aspects, the ultra low dose substance can be administered about 1, 2, 3 or more hours before food is consumed.

It should be understood that the above-mentioned "food effect" methods and uses can further include the use of doxepin, prodrugs or salts of the same in combination with other insomnia or sleep medications. For example, the methods can include the use of one or more of ramelteon, eszopiclone, zolpidem tartrate, zaleplon or the like. Further, the methods can include the use of one or more of 5-HT2 antagonists (such as ketanserin), H3 agonists, orexin antagonists, noradrenergic antagonists, galanin agonists, CRH antagonists, Gaboxadol, other GABA-A direct antagonists, GABA reuptake inhibitors such as tiagabine), growth hormone and growth hormone agonists, estrogen and estrogen agonists, melatonin agonists or the like. Other examples of medications and substances that can be used in combination with ultra low doses as described herein can be found in U.S. Provisional Application No. 60/873,056, filed on Dec. 6, 2006, entitled COMBINATION THERAPY USING LOW-DOSE DOXEPIN FOR THE IMPROVEMENT OF SLEEP; and U.S. Provisional Application No. 60/910,586, filed on Apr. 6, 2007, entitled COMBINATION THERAPY USING LOW-DOSE DOXEPIN FOR THE IMPROVEMENT OF SLEEP; each of which applications is incorporated herein by reference in its entirety.

Pharmaceutical Compositions and Administration

As discussed above, doxepin, pharmaceutically acceptable salts, prodrugs and compositions that include any of the same can be used to treat insomnia in a mammal, including a human. Such compositions can be used alone, in combination with other substances or the compositions can further include the other substances. For example, the substances can include other insomnia or sleep medications, or other medications that treat a primary illness. For example, doxepin, prodrugs or salts of the same can be used or administered with ramelteon, eszopiclone, zolpidem tartrate, zaleplon or the like. Further, doxepin, prodrugs or salts of the same can be administered with one or more of 5-HT2 antagonists (such as ketanserin), H3 agonists, orexin antagonists, noradrenergic antagonists, galanin agonists, CRH antagonists, Gaboxadol, other GABA-A direct antagonists, GABA reuptake inhibitors (such as tiagabine), growth hormone and growth hormone agonists, estrogen and estrogen agonists, melatonin agonists or the like. Other examples of medications and substances that can be used in combination with ultra low doses as described herein can be found in U.S. Provisional Application No. 60/873,056, filed on Dec. 6, 2006, entitled COMBINATION THERAPY USING LOW-DOSE DOXEPIN FOR THE IMPROVEMENT OF SLEEP; and U.S. Provisional Application No. 60/910,586, filed on Apr. 6, 2007, entitled COMBINATION THERAPY USING LOW-DOSE DOXEPIN FOR THE IMPROVEMENT OF SLEEP; each of which applications is incorporated herein by reference in its entirety. Methods of use can include the step of administering a therapeutically effective amount of the composition or a compound(s) to a mammal in need thereof.

Actual dosage levels of the compound(s) in the pharmaceutical compositions may be varied so as to administer an amount of the compound that is effective to achieve the desired therapeutic response for a particular patient. Examples of dosages that can be used are described more fully elsewhere herein.

Suitable routes of administration include oral, buccal, sublingual, transdermal, rectal, topical, transmucosal, or intestinal administration; parenteral delivery, including intramuscular, subcutaneous, intravenous, intramedullary injections, as well as intrathecal, direct intraventricular, intraperitoneal, intranasal, or intraocular injections.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Administration though oral pathways can be accomplished, for example, using a capsule, a tablet, a granule, a spray, a syrup, a liquid, powder, granules, pastes (e.g., for application to the tongue), Oral administration can be accomplished using fast-melt formulations, for example. Pharmaceutical preparations for oral use can be obtained by mixing one or more solid excipient with pharmaceutical compound as described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Pharmaceutical preparations which can be used orally, including sublingually, include for example, liquid solutions, powders, and suspensions in bulk or unit dosage forms. Also, the oral formulations can include, for example, pills, tablets, granules, sprays, syrups, pastes, powders, boluses, pre-measured ampules or syringes, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take any suitable form, for example, tablets or lozenges.

For topical administration, the compound(s) may be formulated for administration to the epidermis as ointments, gels, creams, pastes, salves, gels, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents.

For injection, the compound(s) or compositions may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For administration by inhalation, the compound(s) for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compound(s) may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compound(s) in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition, any of the compounds) and compositions described herein can also be formulated as a depot preparation. Such long acting formulations may be administered by implantation (for example subcutaneously or intramuscularly) or by intramuscular injection. Thus, for example, the compound(s) may be formulated with suitable polymeric or hydrophobic materials (for example as an emulsion in an acceptable oil) or ion exchange resins, or as sparingly soluble derivatives, for example, as a sparingly soluble salt. Furthermore, any of the compound(s) and compositions described herein also can be formulated as a fast-melt preparation. The compound(s) and compositions can also be formulated and administered as a drip, a suppository, a salve, an ointment, an absorbable material such a transdermal patch, or the like.

One can also administer the compound(s) of the invention in sustained release forms or from sustained release drug delivery systems. A description of representative sustained release materials can be found in the incorporated materials in *Remington: The Science and Practice of Pharmacy* ($20^{th}$ ed, Lippincott Williams & Wilkens Publishers (2003)), which is incorporated herein by reference in its entirety.

A variety of techniques for formulation and administration can be found in *Remington: The Science and Practice of Pharmacy* ($20^{th}$ ed, Lippincott Williams & Wilkens Publishers (2003)), which is incorporated herein by reference in its entirety.

Doxepin, pharmaceutically acceptable salts, and/or prodrugs can be included as part of a composition. The compounds and compositions can include any suitable form of the compound for pharmaceutical delivery, as discussed in further detail herein. For example, in certain embodiments, the compounds or compositions comprising the same may include a pharmaceutically acceptable salt of the compound.

The compositions and formulations disclosed herein also can include one or more pharmaceutically acceptable carrier materials or excipients. Such compositions can be prepared for storage and for subsequent administration. Acceptable carriers or diluents for therapeutic use are well known in the pharmaceutical art, and are described, for example, in the incorporated material of *Remington: The Science and Practice of Pharmacy* ($20^{th}$ ed, Lippincott Williams & Wilkens Publishers (2003)), which is incorporated herein by reference in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. Suitable excipients for injectable solutions include, without limitation, water, alcohols, polyols, glycerol, and vegetable oils. The pharmaceutical compositions can additionally include preservatives, solubilizers, stabilizers, wetting agents, emulsifiers, sweeteners, colorants, flavorings, buffers, coating agents, or antioxidants. Sterile compositions for injection can be formulated according to conventional pharmaceutical practice as described in the incorporated material in Remington: The Science and Practice of Pharmacy (20$^{th}$ ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice. The compound can also be made in microencapsulated form. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

The compositions and formulations can include any other agents that provide improved transfer, delivery, tolerance, and the like. These compositions and formulations can include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol. Pharmacol. 32(2): 210-8 (2000), Charman W N "Lipids, lipophilic drugs, and oral drug delivery-some emerging concepts." J. Pharm Sci. 89(8): 967-78 (2000), Powell et al. "Compendium of excipients for parenteral formulations" PDA J Pharm Sci Technol. 52: 238-311 (1998) and the citations therein for additional information related to formulations, excipients and carriers well known to pharmaceutical chemists.

The selected dosage level can depend upon, for example, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. It will be understood, however, that the specific dose level for any particular patient can depend upon a variety of factors including the genetic makeup, body weight, general health, diet, time and route of administration, combination with other drugs and the particular condition being treated, and its severity. For the treatment of insomnia, preferably one dose is administered prior to bedtime.

Dosages

Any suitable dosage of doxepin, a pharmaceutical salt, or prodrug can be used to treat the sleep disorder such as insomnia. In some aspects, daily dosages may vary from about 0.0001 to about 0.49 milligrams, from about 0.001 to about 0.1 milligrams, or from about 0.01 to about 0.099 milligrams. Daily dosages of about 0.2, 0.3, or 0.4 milligrams can be used, for example. Preferably, daily dosages of about 0.01, 0.02, 0.03, 0.04, 0.05, 0.06, 0.07, 0.08, 0.09 or 0.1 milligrams can be utilized. Still in some aspects, a dosage of about 0.001, 0.005, or about 0.008 milligrams may be used. In other aspects, a daily dosage of less than 0.5, less than 0.1 or less than about 0.099 milligrams can be used. However, as it is recognized that each individual may react differently to a given dose of the medication used, the dosages recited should be accorded flexibility. Further, any suitable unit dosage form can be formulated to contain doxepin, a prodrug or a pharmaceutically acceptable salt in the above-recited amounts (e.g., 0.0001-0.49 mg). These low doses have reduced side effects, are surprisingly effective, and have a relatively rapid onset.

Some examples, without limitation of dosages of medications and compounds that can be combined with the ultra low dose compounds described herein can be found in U.S. Provisional Application No. 60/873,056, filed on Dec. 6, 2006, entitled COMBINATION THERAPY USING LOW-DOSE DOXEPIN FOR THE IMPROVEMENT OF SLEEP; and U.S. Provisional Application No. 60/910,586, filed on Apr. 6, 2007, entitled COMBINATION THERAPY USING LOW-DOSE DOXEPIN FOR THE IMPROVEMENT OF SLEEP; each of which applications is incorporated herein by reference in its entirety.

EXAMPLES

Example 1

Synthesis of Doxepin (11-(3-dimethylaminopropylidene)-6,11-dihydrodibenzo-[b,e]-oxepine)

Part (a) A Grignard compound was prepared in the conventional manner from 4.8 g (0.2 gram-atom) magnesium in 100 ml ether and 30 g (34 ml) (3-chloropropyl)-tertbutyl-ether and 16.40 grams (0.078 mol) 6,11-dihydrodibenzo-[b,e]-oxepine-11-one dissolved in 100 ml ether were added in dropwise fashion so that the contents of the flask boiled lightly. The mixture was heated for 1 hour with agitation in a reflux condenser to complete the reaction and then it was decomposed with ammonium chloride solution. The product which was obtained by separating, drying and eliminating the solvent produced, when the ether residue (24.0 g) was extracted with ligroin, amounted to 20.3 g (80.0% of theory) of 11-(3-tertbutoxypropyl)-11-hydroxy-6,11-dihydrodibenzo-[b,e]-oxepine, having a inciting point of 124-126° C. The (3-chloropropyl)-tertbutyl ether was thereafter obtained in the following manner: 19 g (0.2 mol) 1-chloropropanol-(3), 50 ml liquid isobutylene and 0.5 ml concentrated sulfuric acid were permitted to stand for 24 hours in an autoclave, then poured into excess sodium bicarbonate solution and extracted with ether. The ether solution was dried with calcium chloride and distilled. 23.6 grams of (3-chloroproyl)-tertbutylether having a boiling point of 150-156° C. (78% of theory) were recovered.

Part (b) 30.8 grams of the 11-(3-tertbutoxypropyl)-11-hydroxy-6,11-dihydrodibenzo-[b,e]-oxepine obtained according to (a) above and 150 ml absolute alcoholic hydrochloric acid were heated for 1 hour at ebullition. After removing the solvent by evaporation, the residue was crystallized with ligroin, 21.0 grams (88.5% of theory) of 11-(3-hydroxypropylidene)-6,11-dihydrodibenzo-[b,e]-oxepine having a melting point of 108-111° C. were obtained. After recrystallization from acetic acid ester, the compound melted at 112-114° C.

Part (c) 5.0 ml thionyl chloride dissolved in 5 ml benzene were added dropwise at room temperature to 12.6 g (0.05 mol) of the 11-(3-hydroxypropylidene)-6,11-dihydrodibenzo-[b,e]-oxepine obtained in part (b) above. After 1 hour of standing, the contents of the flask were heated at ebullition for 2 hours. The volatile components were thereafter removed and the remainder distilled using high vacuum. The yield amounted to 10.6 g (78.5% of theory) of 11-(3-chloropropylidene)-6,11-dihydrodibenzo-[b,e]-oxepine having a B.P.0.1 169-172° C., a melting point of 106-111° C. After recrystallization from 20 ml of acetic acid ester, 9.1 g (67.5% of theory) of pure product having a melting point of 113-115° C. were obtained. The crude product can however be used quite easily for further processing.

Part (d) 5.4 g (0.02 mol) of the 11-(3-chloropropylidene)-6,11-dihydrodibenzo-[b,e]-oxepine, prepared according to (c) above, in 20 ml tetrahydrofuran and 5.5 g (0.12 mol) dimethylamine in 20 ml ethanol were heated together for 3 hours using a glass autoclave and a temperature of 95-100° C. (boiling water bath). Water and 6 N hydrochloric acid were, added to the contents of the autoclave and the mixture was extracted with ether. The separated, aqueous-acid components were then made alkaline with dilute caustic soda solution, and the oil thereby separated was taken up in ether. The ether residue, after distillation in a high vacuum, produced 4.1 g (73.5% of theory) of 11-(3-dimethylaminopropylidene)-6,11-dihydrodibenzo-[b,e]-oxepine, having a B.P.0.1 147-150° C. The melting point of the hydrochloride was 182-184° C. (recrystallized from isopropanol).

Example 2

A patient suffers from transient or short term insomnia. The patient is otherwise healthy with normal affect with no depression, anxiety or substance overuse. The patient is prescribed doxepin in a daily dosage of 0.4 milligrams, prior to bedtime. Administration of doxepin relieves the insomnia.

Example 3

A patient suffers from transient or short term insomnia. The patient is otherwise healthy with normal affect with no depression, anxiety or substance overuse. The patient is prescribed doxepin in a daily dosage of 0.08 milligrams, prior to bedtime. Administration of doxepin relieves the insomnia.

Example 4

A patient suffers from transient or short term insomnia. The patient is otherwise healthy with normal affect with no depression, anxiety or substance overuse. The patient is prescribed doxepin in a daily dosage of 0.009 milligrams, prior to bedtime. Administration of doxepin relieves the insomnia.

Example 5

A patient suffers from transient or short term insomnia. The patient is otherwise healthy with normal affect with no depression, anxiety or substance overuse. The patient is prescribed doxepin in a daily dosage of 0.0005 milligrams prior to bedtime. Administration of doxepin relieves the insomnia.

Example 6

A patient suffers from transient or short term insomnia. The patient also suffers from depression. The patient is prescribed doxepin in a daily dosage of 0.3 milligrams, prior to bedtime. Administration of doxepin relieves the insomnia.

Example 7

A patient suffers from transient or short term insomnia. The patient also suffers from depression. The patient is prescribed doxepin in a daily dosage of 0.1 milligrams, prior to bedtime. Administration of doxepin relieves the insomnia.

Example 8

A patient suffers from transient or short term insomnia. The patient also suffers from depression. The patient is prescribed doxepin in a daily dosage of 0.006 milligrams, prior to bedtime. Administration of doxepin relieves the insomnia.

Example 9

A patient suffers from transient or short term insomnia. The patient is otherwise healthy with normal affect with no depression, anxiety or substance overuse. The patient is prescribed doxepin in a daily dosage of 0.008 milligrams, prior to bedtime. Administration of doxepin relieves the insomnia.

Example 10

A patient suffers from transient or short term insomnia. The patient also suffers from depression. The patient is prescribed doxepin in a daily dosage of 0.001 milligrams, prior to bedtime. Administration of doxepin relieves the insomnia.

Example 11

A patient suffers from transient or short term insomnia. The patient also suffers from depression. The patient is prescribed doxepin in a daily dosage of 0.0003 milligrams prior to bedtime. Administration of doxepin relieves the insomnia.

Example 12

A patient suffers from chronic insomnia. The patient is otherwise healthy with normal affect with no depression, anxiety or substance overuse. The patient is prescribed doxepin in a daily dosage of 0.4 milligrams prior to bedtime. Administration of doxepin relieves the insomnia.

Example 13

A patient suffers from chronic insomnia. The patient is otherwise healthy with normal affect with no depression, anxiety or substance overuse. The patient is prescribed doxepin in a daily dosage of 0.2 milligrams prior to bedtime. Administration of the doxepin relieves the insomnia.

Example 14

A patient suffers from chronic insomnia. The patient is otherwise healthy with normal affect with no depression, anxiety or substance overuse. The patient is prescribed doxepin in a daily dosage of 0.02 milligrams prior to bedtime. Administration of doxepin relieves the insomnia.

Example 15

A patient suffers from chronic insomnia. The patient is otherwise healthy with normal affect with no depression, anxiety or substance overuse. The patient is prescribed doxepin in a daily dosage of 0.007 milligrams prior to bedtime. Administration of doxepin relieves the insomnia.

Example 16

A patient suffers from chronic insomnia. The patient is otherwise healthy with normal affect with no depression, anxiety or substance overuse. The patient is prescribed doxepin in a daily dosage of 0.009 milligrams prior to bedtime. Administration of doxepin relieves the insomnia.

Example 17

A patient suffers from chronic insomnia. The patient is otherwise healthy with normal affect with no depression, anxiety or substance overuse. The patient is prescribed doxepin in a daily dosage of 0.0002 milligrams prior to bedtime. Administration of doxepin relieves the insomnia.

Example 18

A patient suffers from chronic insomnia. The patient is otherwise healthy with normal affect with no depression, anxiety or substance overuse. The patient is prescribed doxepin in a daily dosage of 0.0002 milligrams prior to bedtime. Administration of doxepin relieves the insomnia.

Example 19

A patient suffers from chronic insomnia. The patient also suffers from depression. The patient is prescribed doxepin in a daily dosage of 0.5 milligram prior to bedtime. Administration of doxepin relieves the insomnia.

Example 20

A patient suffers from chronic insomnia. The patient also suffers from depression. The patient is prescribed doxepin in a daily dosage of 0.03 milligrams prior to bedtime. Administration of doxepin relieves the insomnia.

Example 21

A patient suffers from chronic insomnia. The patient also suffers from depression. The patient is prescribed doxepin in a daily dosage of 0.05 milligrams prior to bedtime. Administration of doxepin relieves the insomnia.

Example 22

A patient suffers from chronic insomnia. The patient also suffers from depression. The patient is prescribed doxepin in a daily dosage of 0.004 milligrams prior to bedtime. Administration of doxepin relieves the insomnia.

Example 23

A patient suffers from chronic insomnia. The patient also suffers from depression. The patient is prescribed doxepin in a daily dosage of 0.0001 milligrams prior to bedtime. Administration of doxepin relieves the insomnia.

Example 24

A patient suffers from chronic insomnia. The patient also suffers from depression. The patient is prescribed doxepin in a daily dosage of 0.0009 milligrams prior to bedtime. Administration of the doxepin relieves the insomnia.

Example 25

A patient suffers from a sleep disorder. The patient is prescribed doxepin in a daily dosage of 0.1 milligram prior to bedtime. Administration of the doxepin relieves the insomnia.

Example 26

A patient suffers from a sleep disorder. The patient is prescribed a pharmaceutically acceptable salt of doxepin in a daily dosage of 0.3 milligrams prior to bedtime. Administration of the pharmaceutically acceptable salt of doxepin relieves the insomnia.

Example 27

A patient suffers from a sleep disorder. The patient is prescribed a pharmaceutically acceptable salt of doxepin in a daily dosage of 0.009 milligrams prior to bedtime. Administration of the pharmaceutically acceptable salt of doxepin relieves the insomnia.

Example 28

A patient suffers from a sleep disorder. The patient is prescribed a pharmaceutically acceptable salt of doxepin in a daily dosage of 0.006 milligrams prior to bedtime. Administration of the pharmaceutically acceptable salt relieves the insomnia.

Example 29

A patient suffers from a sleep disorder. The patient is prescribed a pharmaceutically acceptable salt of doxepin in a daily dosage of 0.0007 milligrams prior to bedtime. Administration of the pharmaceutically acceptable salt of doxepin relieves the insomnia.

Example 30

A patient suffers from a sleep disorder. The patient is prescribed a prodrug of doxepin in a daily dosage of 0.1 milligrams prior to bedtime. Administration of the prodrug relieves the insomnia.

Example 31

A patient suffers from a sleep disorder. The patient is prescribed a prodrug of doxepin in a daily dosage of 0.0006 milligrams prior to bedtime. Administration of the prodrug relieves the insomnia.

Example 32

A patient suffers from a sleep disorder. The patient is prescribed a prodrug of doxepin in a daily dosage of 0.05 milligrams prior to bedtime. Administration of the prodrug relieves the insomnia.

Example 33

A patient suffers from a sleep disorder. The patient is prescribed a prodrug of doxepin in a daily dosage of 0.004 milligrams prior to bedtime. Administration of the prodrug relieves the insomnia.

Example 34

A patient suffers from a sleep disorder. The patient is prescribed a prodrug of doxepin in a daily dosage of 0.0009 milligrams prior to bedtime. Administration of the prodrug relieves the insomnia.

Example 35

Assessment of the Effect of Food on the Pharmacokinetics of Doxepin, a Pharmaceutically Acceptable Salt of Doxepin, or a Prodrug or Doxepin A study assesses the effect of food on the pharmacokinetics (PK) of doxepin, a pharmaceutically acceptable salt of doxepin or a prodrug of doxepin in healthy subjects. Subjects receive ultra low doses of the subject compounds in the morning under either fed or fasted conditions. All subjects are dosed under both fed and fasted conditions during the study.

Subjects being dosed under fasted conditions are required to fast overnight for at least 10 hours prior to study drug administration and for 4 hours after study drug administration. Fluids are restricted from 1 hour predose to 1 hour postdose, except for water taken at the time of dosing. Subjects being dosed under fed conditions are dosed approximately 5 minutes after eating a high-fat, high-calorie standardized breakfast (to be ingested within 25 minutes). Subjects are required to ingest the entire contents of the breakfast. All subjects are required to remain in bed for approximately 4 hours after dosing.

Contents of the high-fat, high-calorie standardized breakfast are:
Two eggs fried in butter;
Two slices of bacon;
240 mL (8 fl. oz) whole milk;
57 g (2 oz) of hash browned potatoes; and
Two slices of toasted white bread with butter.

The total amount of protein, fat, and carbohydrate that make up this meal is approximately 33, 55, and 58 g, respectively. The total calorie content is approximately 850 kcal.

The PK profiles are evaluated. Blood samples are collected at predose (0 hour) and at various postdose time points (e.g., 0.08, 0.17, 0.25, 0.5, 0.75, 1, 1.5, 2, 3, 4, 6, 8, 12, 24, 36, 48, 60, 72, and 96 hours postdose). The samples are analyzed for concentrations of the test compound in plasma. Plasma concentrations are measured using validated high performance liquid chromatography coupled to tandem mass spectrometry. The following PK parameters are estimated by noncompartmental methods using actual elapsed time from dosing:

$C_{max}$ (ng/mL) Maximum observed plasma concentration, obtained directly from the observed concentration versus time data.

$T_{max}$ (h) Time to maximum plasma concentration, obtained directly from the observed concentration versus time data.

$AUC_{0-\infty}$ (ng·h/mL) Area under the curve from time zero extrapolated to infinity, calculated by linear up/log down trapezoidal summation and extrapolated to infinity by addition of the last quantifiable concentration divided by the elimination rate constant $(AUC_{0-Tlast}+C_{last}/\lambda_z)$. If the extrapolated area $(C_{last}/\lambda_z)$ was greater than 30% of $AUC_{0-\infty}$, then $AUC_{0-\infty}$ was set to missing.

$AUC_{0-Tlast}$ (ng·h/mL) Area under the curve from time zero to time of last measurable concentration, calculated by linear up/log down trapezoidal summation.

$AUC_{0-24}$ (ng·h/mL) Area under the curve from time zero until 24 hours, calculated by linear up/log down trapezoidal summation. If the 24 h sample was missing or below the lower limit of quantification, $AUC_{0-Tlast}$ was to be reported as $AUC_{0-24}$.

$AUC_{0-48}$ (ng·h/mL) Area under the curve from time zero until 48 hours, calculated by linear up/log down trapezoidal summation. If the 48 h sample was missing or below the lower limit of quantification, $AUC_{0-Tlast}$ was to be reported as $AUC_{0-48}$.

$AUC_{0-72}$ (ng·h/mL) Area under the curve from time zero until 72 hours, calculated by linear up/log down trapezoidal summation. If the 72 h sample was missing or below the lower limit of quantification, $AUC_{0-Tlast}$ was to be reported as $AUC_{0-72}$.

$AUC_{0-96}$ (ng·h/mL) Area under the curve from time zero until 96 hours, calculated by linear up/log down trapezoidal summation. If the 96 h sample was missing or below the lower limit of quantification, $AUC_{0-Tlast}$ was to be reported as $AUC_{0-96}$.

$\lambda_z$ (1/h) Elimination rate constant associated with the terminal (log linear) portion of the curve. This was estimated via linear regression of time versus log concentration. Visual assessment was used to identify the terminal linear phase of the concentration-time profile. A minimum of three data points were used for determination.

$t_{1/2}$ (h) Apparent terminal half-life, determined as $\ln 2/\lambda_z$.
CL/F (L/h) Apparent oral clearance, calculated as dose divided by $AUC_{0-\infty}$.
Vd/F (L) Apparent volume of distribution, calculated as $(CL/F)/\mu_z$.

Many modifications and variations of the embodiments described herein may be made without departing from the scope, as is apparent to those skilled in the art. The specific embodiments described herein are offered by way of example only.

What is claimed is:

1. A composition comprising doxepin, or a pharmaceutically acceptable salt thereof in a dosage of about 0.0001 milligrams to about 0.4 milligrams.

2. The composition of claim 1, further comprising a pharmaceutically acceptable carrier.

3. The composition of claim 1, wherein the pharmaceutically acceptable salt of doxepin is the hydrochloride salt thereof.

4. The composition of claim 1, comprising a dosage of about 0.001 to about 0.1 milligrams of doxepin, or a pharmaceutically acceptable salt of doxepin.

5. The composition of claim 1, comprising a dosage of about 0.01 to about 0.099 milligrams of doxepin, or a pharmaceutically acceptable salt of doxepin.

6. The composition of claim 1, wherein the composition is in a form suitable for oral or nasal administration.

7. The composition of claim 1, further comprising at least one of ramelteon, eszopiclone, zolpidem tartrate, or zaleplon.

8. The composition of claim 1, further comprising at least one additional sleep medication.

9. The composition of claim 8, Wherein the at least one additional sleep medication is selected from a 5-HT2 antagonist, ketanserin, a H3 agonist, an orexin antagonist, a noradrenergic antagonist, a galanin agonist, a CRH antagonist, Gaboxadol, a GABA-A direct antagonist, a GABA reuptake inhibitor, tiagabine, a growth hormone, a growth hormone agonist, estrogen, an estrogen agonist, or a melatonin agonist.

* * * * *